United States Patent
Bikko

(10) Patent No.: US 9,779,751 B2
(45) Date of Patent: Oct. 3, 2017

(54) RESPIRATORY BIOFEEDBACK DEVICES, SYSTEMS, AND METHODS

(75) Inventor: Nirinjan Bikko, Walnut Creek, CA (US)

(73) Assignee: BREATH RESEARCH, INC., Walnut Creek, CA (US)

(*) Notice: Subject to any disclaimer, the term of this patent is extended or adjusted under 35 U.S.C. 154(b) by 1028 days.

(21) Appl. No.: 12/709,370

(22) Filed: Feb. 19, 2010

(65) Prior Publication Data

US 2010/0240945 A1 Sep. 23, 2010

Related U.S. Application Data

(63) Continuation-in-part of application No. 11/645,207, filed on Dec. 21, 2006.

(Continued)

(51) Int. Cl.
*A61B 5/08* (2006.01)
*G10L 21/00* (2013.01)
(Continued)

(52) U.S. Cl.
CPC .......... *G10L 21/00* (2013.01); *A61B 5/02405* (2013.01); *A61B 5/08* (2013.01); *A61B 5/1112* (2013.01); *A61B 5/486* (2013.01); *A61B 5/7415* (2013.01); *A61B 7/003* (2013.01); *A61F 5/56* (2013.01); *A61B 5/01* (2013.01); *A61B 5/021* (2013.01); *A61B 5/024* (2013.01); *A61B 5/0205* (2013.01); *A61B 5/0476* (2013.01); *A61B 5/145* (2013.01); *A61B 5/14532* (2013.01); *G06F 19/345* (2013.01); *G06F 19/3406* (2013.01)

(58) Field of Classification Search
CPC ....... A61B 5/486; A61B 7/003; A61B 5/7264; A61B 5/08; A61B 5/0816; A61B 5/4812
USPC .................................................. 600/529–543
See application file for complete search history.

(56) References Cited

U.S. PATENT DOCUMENTS 3,991,304 A 11/1976 Hillsman
4,063,550 A 12/1977 Tiep
(Continued)

FOREIGN PATENT DOCUMENTS

EP 0 145 160 A2 6/1985
EP 0804938 11/1997
(Continued)

OTHER PUBLICATIONS

Extended European Search Report mailed Aug. 8, 2011 in EP Application No. 06 84 9045, 7 pages.

*Primary Examiner* — Patricia Mallari
*Assistant Examiner* — Karen Toth

(57) ABSTRACT

Respiratory-based biofeedback devices, systems, and methods are provided. A respiratory biofeedback method includes producing a respiratory signal in response to a user's respiratory activity, generating an audio output signal that includes a modified version of the respiratory signal, and converting the audio output signal into sound waves output to the user to provide biofeedback. The sound waves can be output to the user in real time response to the user's respiratory activity. A microphone can be used to generate the respiratory signal. The generated audio output signal can includes the respiratory signal modified to increase a volume level of a portion of the respiratory signal where the volume level exceeds a specified volume level.

49 Claims, 8 Drawing Sheets

Related U.S. Application Data

(60) Provisional application No. 60/754,824, filed on Dec. 28, 2005.

(51) Int. Cl.
| | |
|---|---|
| *A61B 5/11* | (2006.01) |
| *A61B 5/00* | (2006.01) |
| *A61B 7/00* | (2006.01) |
| *A61F 5/56* | (2006.01) |
| *A61B 5/01* | (2006.01) |
| *A61B 5/0205* | (2006.01) |
| *A61B 5/021* | (2006.01) |
| *A61B 5/024* | (2006.01) |
| *A61B 5/0476* | (2006.01) |
| *A61B 5/145* | (2006.01) |
| *G06F 19/00* | (2011.01) |

(56) References Cited

U.S. PATENT DOCUMENTS

| | | | |
|---|---|---|---|
| 4,064,869 A | 12/1977 | Defares et al. | |
| 4,143,648 A | 3/1979 | Cohen et al. | |
| 4,215,431 A | 7/1980 | Nady | |
| 4,220,142 A | 9/1980 | Rosen et al. | |
| 4,337,445 A | 6/1982 | Akagiri | |
| 4,644,330 A | 2/1987 | Dowling | |
| 4,798,538 A | 1/1989 | Yagi | |
| 4,848,360 A | 7/1989 | Palsgard et al. | |
| 4,924,876 A * | 5/1990 | Cameron | 600/538 |
| 4,981,295 A | 1/1991 | Belman et al. | |
| 5,076,281 A * | 12/1991 | Gavish | 600/534 |
| 5,137,501 A | 8/1992 | Mertesdorf | |
| 5,444,786 A | 8/1995 | Raviv | |
| 5,477,667 A | 12/1995 | Bryant | |
| 5,477,867 A | 12/1995 | Balkanyi | |
| 5,633,473 A | 5/1997 | Mori et al. | |
| 5,779,484 A | 7/1998 | Lampotang et al. | |
| 5,800,337 A * | 9/1998 | Gavish | 600/27 |
| 5,810,722 A | 9/1998 | Heikkila | |
| 5,879,313 A * | 3/1999 | Raviv et al. | 600/595 |
| 5,899,203 A | 5/1999 | Defares et al. | |
| 5,936,464 A | 8/1999 | Grondahl | |
| 6,027,463 A | 2/2000 | Moriyasu | |
| 6,056,703 A | 5/2000 | Sandler et al. | |
| 6,064,964 A | 5/2000 | Yamamoto et al. | |
| 6,090,037 A | 7/2000 | Gavish | |
| 6,134,331 A | 10/2000 | Bækgaard | |
| 6,142,950 A | 11/2000 | Allen et al. | |
| 6,261,238 B1 * | 7/2001 | Gavriely | 600/532 |
| 6,273,728 B1 | 8/2001 | Van Meurs et al. | |
| 6,411,850 B1 | 6/2002 | Kay et al. | |
| 6,423,013 B1 | 7/2002 | Bakker et al. | |
| 6,626,843 B2 | 9/2003 | Hillsman | |
| 6,662,032 B1 * | 12/2003 | Gavish et al. | 600/323 |
| 6,889,033 B2 | 5/2005 | Bongfeldt | |
| 6,935,335 B1 | 8/2005 | Lehrman et al. | |
| 7,006,650 B1 | 2/2006 | Wild | |
| 7,390,304 B2 | 6/2008 | Chen et al. | |
| 7,554,028 B2 | 6/2009 | Fujii | |
| 7,559,903 B2 | 7/2009 | Moussavi et al. | |
| 7,785,249 B2 * | 8/2010 | Schachter et al. | 600/27 |
| 8,092,381 B2 | 1/2012 | Edwards | |
| 8,768,489 B2 | 7/2014 | Thieberger et al. | |
| 8,834,364 B2 | 9/2014 | Heneghan et al. | |
| 2002/0090921 A1 | 7/2002 | Midtgaard et al. | |
| 2003/0072457 A1 | 4/2003 | Grasfield et al. | |
| 2003/0130595 A1 | 7/2003 | Mault | |
| 2003/0212338 A1 * | 11/2003 | Linck et al. | 600/538 |
| 2004/0186390 A1 | 9/2004 | Ross et al. | |
| 2004/0225226 A1 | 11/2004 | Lehrman et al. | |
| 2004/0260191 A1 * | 12/2004 | Stubbs et al. | 600/520 |
| 2005/0032496 A1 | 2/2005 | Saeki | |
| 2005/0068211 A1 | 3/2005 | Arai et al. | |
| 2005/0124906 A1 | 6/2005 | Childre et al. | |
| 2005/0192508 A1 * | 9/2005 | Lange et al. | 600/534 |
| 2006/0009971 A1 | 1/2006 | Kushner et al. | |
| 2006/0063981 A1 | 3/2006 | Sotos et al. | |
| 2006/0107824 A1 | 5/2006 | Bando et al. | |
| 2006/0198533 A1 | 9/2006 | Wang et al. | |
| 2007/0117075 A1 | 5/2007 | Gordon et al. | |
| 2007/0167855 A1 | 7/2007 | Shin et al. | |
| 2007/0173730 A1 | 7/2007 | Bikko | |
| 2007/0239225 A1 * | 10/2007 | Saringer | 607/42 |
| 2007/0282174 A1 * | 12/2007 | Sabatino | 600/300 |
| 2007/0282212 A1 | 12/2007 | Sierra et al. | |
| 2008/0071137 A1 | 3/2008 | Schachter et al. | |
| 2008/0082017 A1 | 4/2008 | Savic | |
| 2008/0109965 A1 * | 5/2008 | Mossbeck | 5/713 |
| 2009/0118631 A1 | 5/2009 | Gavish et al. | |
| 2009/0312660 A1 | 12/2009 | Guarino et al. | |
| 2010/0069774 A1 | 3/2010 | Bingham et al. | |
| 2010/0174200 A1 | 7/2010 | Wood et al. | |
| 2010/0262031 A1 | 10/2010 | Fu et al. | |
| 2011/0125045 A1 | 5/2011 | Scholz et al. | |
| 2011/0230778 A1 | 9/2011 | Lai et al. | |
| 2011/0295138 A1 | 12/2011 | Lai et al. | |
| 2011/0295139 A1 | 12/2011 | Yang et al. | |
| 2012/0065978 A1 | 3/2012 | Villavicencio | |
| 2012/0071777 A1 | 3/2012 | MacAuslan | |
| 2014/0155773 A1 | 6/2014 | Stamatopoulos et al. | |
| 2014/0350361 A1 | 11/2014 | De Chazal et al. | |

FOREIGN PATENT DOCUMENTS

| | | |
|---|---|---|
| EP | 2925217 | 10/2015 |
| JP | 52-41993 S | 3/1977 |
| WO | 98/14116 A2 | 4/1998 |
| WO | WO0123040 | 4/2001 |
| WO | 2005/089856 A1 | 9/2005 |
| WO | WO2011132118 | 10/2011 |
| WO | WO2014083079 | 6/2014 |

\* cited by examiner

RESPIRATORY BIOFEEDBACK DEVICES, SYSTEMS, AND METHODS

CROSS-REFERENCE TO RELATED APPLICATION

This application is a continuation-in-part of U.S. patent application Ser. No. 11/645,207, filed on Dec. 21, 2006; which claims priority to U.S. Provisional Application No. 60/754,824, filed Dec. 28, 2005, the full disclosures of which are incorporated herein by reference.

BACKGROUND

Biofeedback devices, systems, and methods are provided. In many embodiments, the disclosed biofeedback devices, system, and methods generate an audio output signal that is converted into sound waves output to a user in real time response to the user's respiratory activity. The audio output signal can include a modified version of a respiratory signal generated in response to the user's respiratory activity. For example, a microphone can be used to convert sound of the user's respiratory activity into the respiratory signal, and the respiratory signal can be modified to increase the volume level of portions of the respiratory signal where the volume level exceeds a specified volume level, which may provide the user with the ability to, for example, learn to modify and control breathing sound levels and patterns while awake or asleep. The respiratory signal can also be modified in response to a non-respiratory signal generated in response to a non-respiratory activity of the user, which may provide the user with the ability to, for example, learn to modify and control the non-respiratory activity.

Various respiration biofeedback techniques and systems have been proposed. For example, U.S. Pat. No. 4,924,876 discloses a nasal breath monitor, which uses separate sensors for each nostril to detect the flow of the breath, electronic circuitry to amplify and enhance the detected signal, and stereo headphones to bring this information to the ears. The disclosed electronic circuitry includes a compressor to make quiet breath sounds louder and loud breath sounds quieter, so that the user can hear very gentle breathing without the user being deafened by the explosive turbulence of a sneeze. However, the nasal breath monitor does not accentuate portions of the user's respiratory activity that exceed a specified intensity level. In contrast, the nasal breath monitor accentuates a portion of the user's respiratory activity that does not exceed a specified intensity level. As such, the nasal breath monitor is not operable to accentuate a portion of the user's respiratory activity that exceeds a specified intensity level (e.g., snoring louder than a given threshold).

U.S. Pat. No. 5,477,867 discloses a device for the suppression of snoring. The disclosed device includes a snoring detector, a sound generator to generate a plurality of acoustic signals having differing spectral composition, and a control means for automatically selecting a succession of the acoustic signals generated upon detection of snoring noises. A signal from a microphone is input into the snoring detector, which output a signal to the control means. The control means controls the sound generator, which outputs an acoustic signal to an amplifier, which is also controlled by the control means. The output from the amplifier is converted into sound output to the user. Preferably, the sounds output to the user become increasingly unpleasant as the snoring continues. The output signal from the sound generator does not include a modified version of the audio signal generated by the microphone, which does not increase awareness of the user's respiratory activity as a means of making a change in a breathing pattern.

The recording of breathing sounds in general may be known. For example, U.S. Pat. No. 6,261,238 discloses the use of multiple sensors to analyze breath sounds. The focus of this patent appears to be on the initial screening, detection, defining, and verification process. However, this device does not feedback the sound of the breath to the patient/client for the purpose of education, modification, and training.

U.S. Pat. No. 6,064,964 discloses a data processing apparatus having breath detection function and an image display control method using breath detection. Breathing sound inputted by an input means such as a microphone are detected and used to control a display state of an image on a display screen or a driving state of a movable object such as a robot. However, this device does not feedback the sound of the breath to the patient/client for the purpose of education, modification, and training.

U.S. Pat. No. 6,090,037 discloses devices, systems and methods for the modification of biorhythmic activity. A sensor monitors a user's biorhythmic activity to generate a signal supplied to a monitor that processes the signal to generate output parameters. The output parameters are input into a driver and into a biorhythmic activity modifier. The driver generates modifier operational commands that are input into the biorhythmic activity modifier. The biorhythmic activity modifier modifies the received parameters in accordance with the received modifier operational commands to generate modified output parameters, which are used by the biorhythmic activity modifier to generate the stimulus input to the user. However, this device does not feedback the sound of the breath to the patient/client for the purpose of education, modification, and training.

U.S. Pat. No. 7,006,650 discloses a device for attenuating sound on the human ear, especially for preventing sleep disturbances caused by noise and other sounds. The device includes two sound attenuating ear plugs having miniature integral radio receivers, and a radio station configured to transmit radio signals to the radio receivers for conversion to sound output to the user. The radio station is coupled with various alarm modules (e.g., movement detector, telephone, door bell, baby monitoring device, smoke alarm) to trigger the transmission of specific radio signals from the radio station that are converted into sound output to the user. The radio station also includes a microphone that picks up sounds that can be used to generate corresponding radio signals. For example, the snoring sounds of the user can be picked up. The snoring sound can be evaluated, identified, and used to trigger the transmission of a radio signal to the radio receivers, and the user perceives the corresponding audio signals. The volume of the audio signals is selected such that the snorer is either woken up or urged to change the user's sleeping position and so stop snoring. Apart from artificially generated sounds, the original snoring sounds can be reproduced identically as the audio signals, so that the snoring person hears their own snoring in a kind of sound feedback and interrupts the snoring process. To check whether snoring or another sound is an event, a sound recognition system is arranged between the microphone and the radio station transmitter. Due to the sound recognition system, only certain sounds, which can be specified before hand, are transmitted from the radio station to the radio receivers. As such, this device does not feedback the sound of the breath to the patient/client for the purpose of education, modification, and training.

There is therefore a need for respiratory biofeedback devices, system, and methods that do not suffer from the above and other shortcomings.

BRIEF SUMMARY

Biofeedback devices, systems, and methods are provided. In many embodiments, the respiratory activity of a user is sensed and sounds are output to the user that are based on the sensed respiratory activity. In many embodiments, the output sounds accentuate an undesirable aspect of the user's respiratory activity. For example, a microphone can be used to convert sound of the user's respiratory activity into a respiratory signal. The respiratory signal can then be processed to identify if volume levels of the respiratory activity exceed a desired sound level, and if so, by how much. The respiratory signal can then be modified to amplify the sound levels of the respiratory activity that exceed the desired sound level. The modified respiratory signal can then be incorporated into an output audio signal that is converted into sound waves output to the user. The amplified sound levels of the portions of the respiratory activity that exceed the desired sound level may serve to make the user more aware of the undesirably load respiratory activity, and thereby may help the user to improve the user's respiratory activity. For example, such an approach may be particularly beneficial when used to combat snoring by feeding back an amplified version of the sound of the user snoring to the user, which may help to train the user to control the snoring, which may in turn help improve the sleep quality of the user, as well as the sleep quality of anyone else within hearing range of the user.

The disclosed biofeedback devices, systems, and methods can include additional features and/or functionality. For example, an audio source can be used to generate a secondary audio signal that can be added into the output audio signal, for example, audio instructions from a coach. One or more other physiological sensors (e.g., a heart sensor(s), a brainwave sensor(s), a temperature sensor(s), a muscle tension sensor(s), an arterial pressure sensor(s), an oxygen sensor(s), a glucose sensor(s), a medical imaging device(s)) can be used to gather additional physiological data from the user. The additional physiological data can be analyzed to, for example, provide a basis to determine what portion of the user's respiratory activity to accentuate, and/or by how much. A global positioning satellite (GPS) system receiver can be used to track the user's location. A processor can be used to analyze the acquired sensor data and generate the audio output signal in response to the acquired sensor data. The data can be statistically analyzed and stored in electronic memory for future reference. The sensor signal(s) and/or the audio output signal can be used to generate a kinesthetic output for a kinesthetic output device so as to supplement the audio output. Likewise, the sensor signal(s) can be used to generate a visual output for a display so as to supplement the audio output. Raw and/or processed sensor data can be stored in a memory device for future reference. Such biofeedback devices, systems, and methods can be used in conjunction with one or more users, and can be implemented in standalone devices and/or in a distributed environment such as the interne.

Thus, in a first aspect, a breathing biofeedback device is provided. The breathing biofeedback device has a microphone configured to acquire sounds of a user's breathing; a controller communicatively connected with the microphone, the controller processing the signals acquired by the microphone to produce an output signal, the controller processing the signal whereby the microphone signal is first pre-amplified to a voltage level that can be processed by an audio envelope detector circuit, the envelope detector signal is then fed into the analog-to-digital converter input of the controller allowing it to constantly sample the input volume level, the controller then controlling the output volume level fed to the headphones utilizing a digitally controlled variable-gain amplifier, wherein the output signal is not modified in any manner from the original input, except in volume; and a pair of earphones connected with the controller and configured to convey the output signal to the user while preventing sound leakage that could cause undesirable acoustic feedback. The earphones are preferably configured to stay physically in place while the user is sitting, lying, in motion and sleeping.

In another aspect, a biofeedback method is provided. The biofeedback method includes producing a respiratory signal in response to a user's respiratory activity, generating an audio output signal that includes a modified version of the respiratory signal, and converting the audio output signal into sound waves output to the user to provide biofeedback. In many embodiments, the sound waves are output to the user in real time response to the user's respiratory activity. In many embodiments, the audio output signal is generated by using a digital processor.

In many embodiments, the biofeedback method includes one or more additional steps. For example, the method can further include producing a secondary audio signal, and adding the secondary audio signal to the audio output signal. The method can further include storing data in a memory device. The stored data can include at least one of the respiratory signal, data derived from the respiratory signal, the audio output signal, or data derived from the audio output signal. The method can further include determining one or more locations for the user, for example, via a global positioning satellite (GPS) system receiver, and storing the one or more locations in a memory device. The method can further include generating a kinesthetic output in response at least one of the respiratory signal or the audio output signal. The method can further include generating a visual output in response to at least one of the respiratory signal or the audio output signal.

The respiratory signal can be modified in various ways. For example, the respiratory signal can be modified based on a characteristic other than intensity. The respiratory signal can be modified based on a numerical calculation. The respiratory signal modification can change based on a detected state (e.g., a detected state of the user such as a state of the user's respiratory activity). The respiratory signal can be modified to enhance, accentuate, and/or amplify a portion of the respiratory signal. The respiratory signal can be modified to accentuate a portion of the respiratory signal having an intensity level above a specified intensity level. A microphone, for example, can be used to convert sound of the user's respiratory activity to produce the respiratory signal. The audio output signal can includes the respiratory signal modified to increase a volume level of a portion of the respiratory signal where the volume level exceeds a specified volume level.

The audio output signal can be transmitted to another device for processing, analysis, and/or storage in memory. For example, the audio output signal can be generated by using a first device and the method can further include transmitting the respiratory signal and/or the audio output signal to a second device for processing, analysis, and/or storage in memory. The transmission can occur over a communication network (e.g., interne, phone line, wireless communication network, and the like).

The biofeedback can be provided for a variety of purposes. For example, the biofeedback can be used for education, behavioral modification, stress reduction, snoring reduction, and/or training (e.g., fitness training).

In many embodiments, an article is provided that includes a storage medium having instructions stored thereon, which instructions when executed result in the performance of the above described biofeedback method. The execution of the instructions can also result in the performance of any one or combination of the above-described associated embodiments.

In another aspect, a biofeedback method is provided. The biofeedback method includes producing a respiratory signal in response to a user's respiratory activity, generating a non-respiratory signal in response to a non-respiratory physiological activity of the user, quantifying an aspect of the non-respiratory signal, generating an audio output signal that includes the respiratory signal modified in response to the quantified aspect of the non-respiratory signal, and converting the audio output signal to sound waves output to the user to provide biofeedback. In many embodiments, the sound waves are output to the user in real time response to the user's respiratory activity. In many embodiments, the step of generating a respiratory signal includes converting sound of the user's respiratory activity into the respiratory signal.

In many embodiments, the biofeedback method includes one or more additional steps. For example, the method can further include storing data in a memory device. The stored data can include at least one of the respiratory signal, data derived from the respiratory signal, the non-respiratory signal, data derived from the respiratory signal, the audio output signal, or data derived from the audio output signal. The method can further include producing a secondary audio signal, and can further include adding the secondary audio signal to the audio output signal. The method can further include determining one or more locations for the user, for example, via a global positioning satellite (GPS) system receiver, and storing the one or more locations in a memory device. The method can further include generating a kinesthetic output in response at least one of the respiratory signal, the non-respiratory signal, or the audio output signal. The method can further include generating a visual output in response to at least one of the respiratory signal, the non-respiratory signal, or the audio output signal.

In many embodiments, an article is provided that includes a storage medium having instructions stored thereon, which instructions when executed result in the performance of the above described biofeedback method. The execution of the instructions can also result in the performance of any one or combination of the above-described associated embodiments.

In another aspect, a biofeedback system is provided. The biofeedback system includes a respiratory sensor configured to generate a respiratory signal in response to a user's respiratory activity, a processing unit communicatively coupled with the respiratory sensor, and an audio output device communicatively coupled with the processing unit. The processing unit includes a processor and a tangible medium. The tangible medium includes instructions that when executed cause the processor to generate an audio output signal that includes a modified version of the respiratory signal. The audio device converts the audio output signal to sound waves output to the user to provide biofeedback. In many embodiments, the respiratory signal is modified to accentuate a portion of the respiratory signal having an intensity level above a specified intensity level. In many embodiments, the sound waves are output to the user in real time response to the user's respiratory activity. In many embodiments, the respiratory sensor comprises a microphone. In many embodiments, the generated audio output signal includes the respiratory signal modified to increase a volume level of a portion of the respiratory signal where the volume level exceeds a specified volume level. In many embodiments, the biofeedback system includes an audio source configured to generate a secondary audio signal that is added to the audio output signal.

In many embodiments, the biofeedback system includes one or more additional output devices. For example, the system can include a kinesthetic output device communicatively coupled with the processing unit. The tangible medium can include instructions that when executed cause the processor to generate a kinesthetic output for the kinesthetic output device in response to at least one of the respiratory signal or the audio output signal. The system can include a display communicatively coupled with the processing unit. The tangible medium can include instructions that when executed cause the processor to generate a visual output for the display in response to at least one of the respiratory signal or the audio output signal.

In many embodiments, the biofeedback system includes a memory device. The tangible medium can include instructions that when executed cause the processor to store data in the memory device. The stored data can include at least one of the respiratory signal, data derived from the respiratory signal, the audio output signal, or data derived from the audio output signal.

In many embodiments, the biofeedback system includes capabilities for detecting the location or movement of a user, such as a global positioning satellite (GPS) system receiver communicatively coupled with the processing unit and a memory device communicatively coupled with the processing unit. The GPS receiver can determine one or more locations for the user. The tangible medium can include instructions that when executed cause the processor to store the one or more locations in the memory device.

In another aspect, a biofeedback method is provided. In many embodiments, the above-described biofeedback system can be used to practice the biofeedback method. The biofeedback method includes producing a respiratory signal with a respiratory sensor in response to a user's respiratory activity, transmitting the respiratory signal to a processing unit, generating an audio output signal with the processing unit, transmitting the audio output signal to an audio output device, and converting the audio output signal with the audio output device to sound waves broadcast to the user to provide biofeedback. In many embodiments, the processing unit includes a processor and a tangible medium comprising instructions that when executed cause the processor to generate the audio output signal, with the audio output signal including a modified version of the respiratory signal. In many embodiments, converting the audio output signal into sound waves broadcast to the user is accomplished in real time response to the user's respiratory activity. In many embodiments, producing the respiratory signal with a respiratory sensor includes converting sounds of the user's respiratory activity with a microphone.

In many embodiments, the biofeedback method includes one or more additional steps. For example, the method can include producing a secondary audio signal that is added to the audio output signal. The method can include generating a kinesthetic output for a kinesthetic output device with the processing unit in response to at least one of the respiratory signal or the audio output signal. The method can include generating a visual output for a display with the processing unit in response to at least one of the respiratory signal or the audio output signal. The method can include determining a location for the user, and can include storing the location in a memory device communicatively coupled with the processing unit. The method can include storing data in a memory device coupled with the processing unit. The stored data can include the respiratory signal, data derived from the respiratory signal, the audio output signal, and/or data derived from the audio output signal.

Generating the audio output signal with the processing unit can be accomplished in various ways. For example, the generation of the audio output signal can include accentuating a portion of the respiratory signal having an intensity level above a specified intensity level. The generation of the audio output signal can include increasing a volume level of portions of the respiratory signal where a volume exceeds a specified volume level.

For a further understanding of the nature and advantages of the invention, reference should be made to the following description taken in conjunction with the accompanying drawings.

DETAILED DESCRIPTION

The present invention is directed towards respiratory related biofeedback devices, systems, and methods. Such biofeedback devices, systems, and methods can generate a respiratory signal in response to a user's respiratory activity (e.g., ordinary non-verbal sounds and/or motions of respiration, including snoring) for analysis, interpretation, and feedback to regulate and modify the user's respiratory patterns for health, fitness, performance and general well being. In many embodiments, a self-contained, wearable biofeedback device is provided. In many embodiments, a biofeedback system is provided that can interact with one or more users. In many embodiments, a biofeedback method is provided. Such biofeedback devices, systems, and methods can be used by a user, for example, to learn to modify and control breathing sound levels and patterns while awake or asleep.

Respiratory Biofeedback Devices

Figure 1:
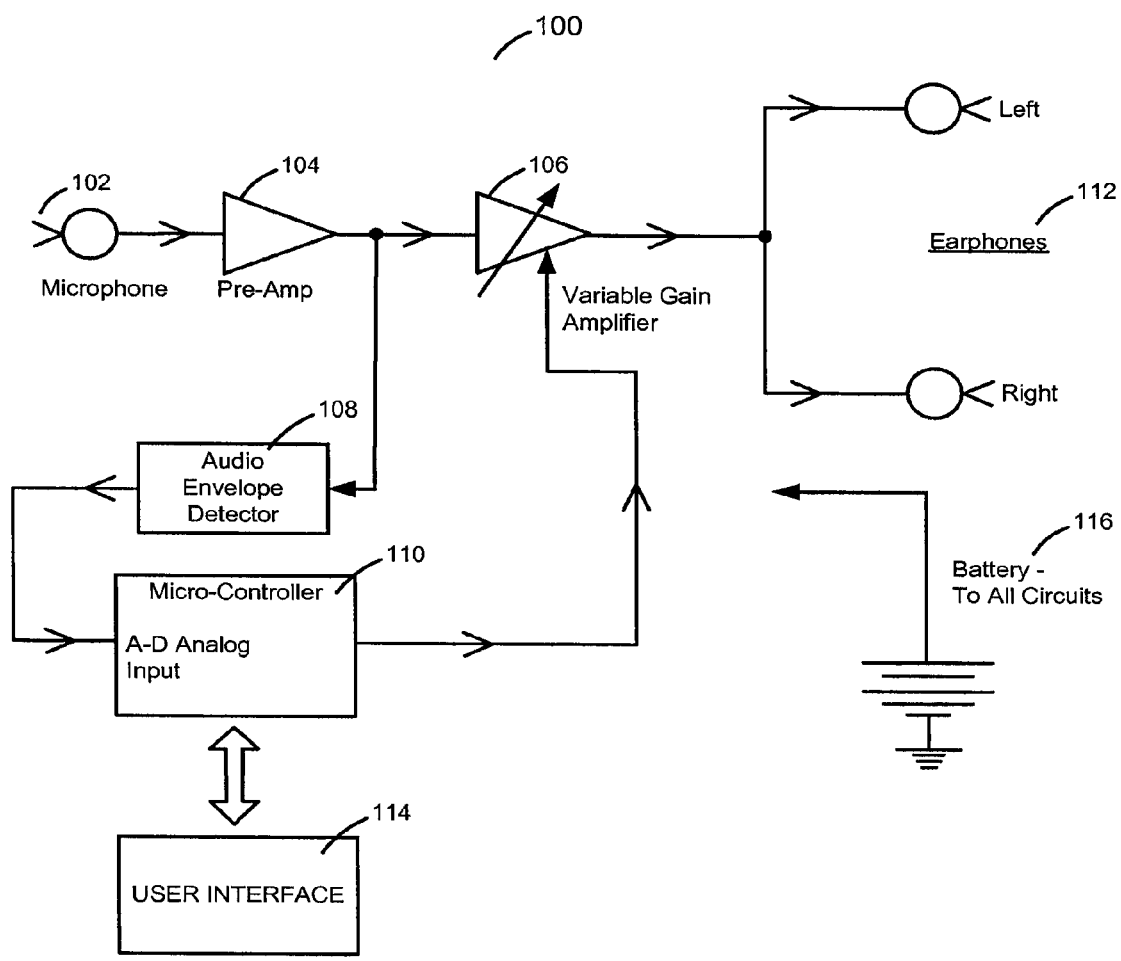
FIG. 1 schematically illustrates a breathing biofeedback device in accordance with many embodiments.

FIG. 1 shows an exemplary circuit diagram 100 of one embodiment of the breathing biofeedback device in accordance with the present invention. As is shown in FIG. 1, the device includes a microphone 102 that is used as an input device for receiving a user's breath sounds. The microphone 102 is connected via the preamp 104 to a variable gain amplifier 106. One output of the preamp is fed to an audio envelope detector 108. The output of the audio envelope detector 108 is fed to a controller that can set the gain for the variable gain amplifier 106. The output of the variable gain amplifier 106 is fed to the speakers or earphones 112. The device also includes a user interface 114 having a display configured to interact with the user. The device also includes an appropriate power supply 116.

In one implementation, the breathing biofeedback device can be a small battery-powered device that is partly worn on the user's head (e.g., using a headband) in a comfortable manner. There can be a connector from the headband to a display unit where settings can be made and viewed. There can also be a remote control to modify settings. As described above, the breathing biofeedback device can include various subcomponents. These include an input device, an output device, a display unit, a controller or processor, and a user interface that is displayed on the display unit and with which the user or wearer interacts. In addition, the device can include a memory device that can be used to aid the operation of the processor and also to store and delete various received or processed signals or information.

Figure 2:
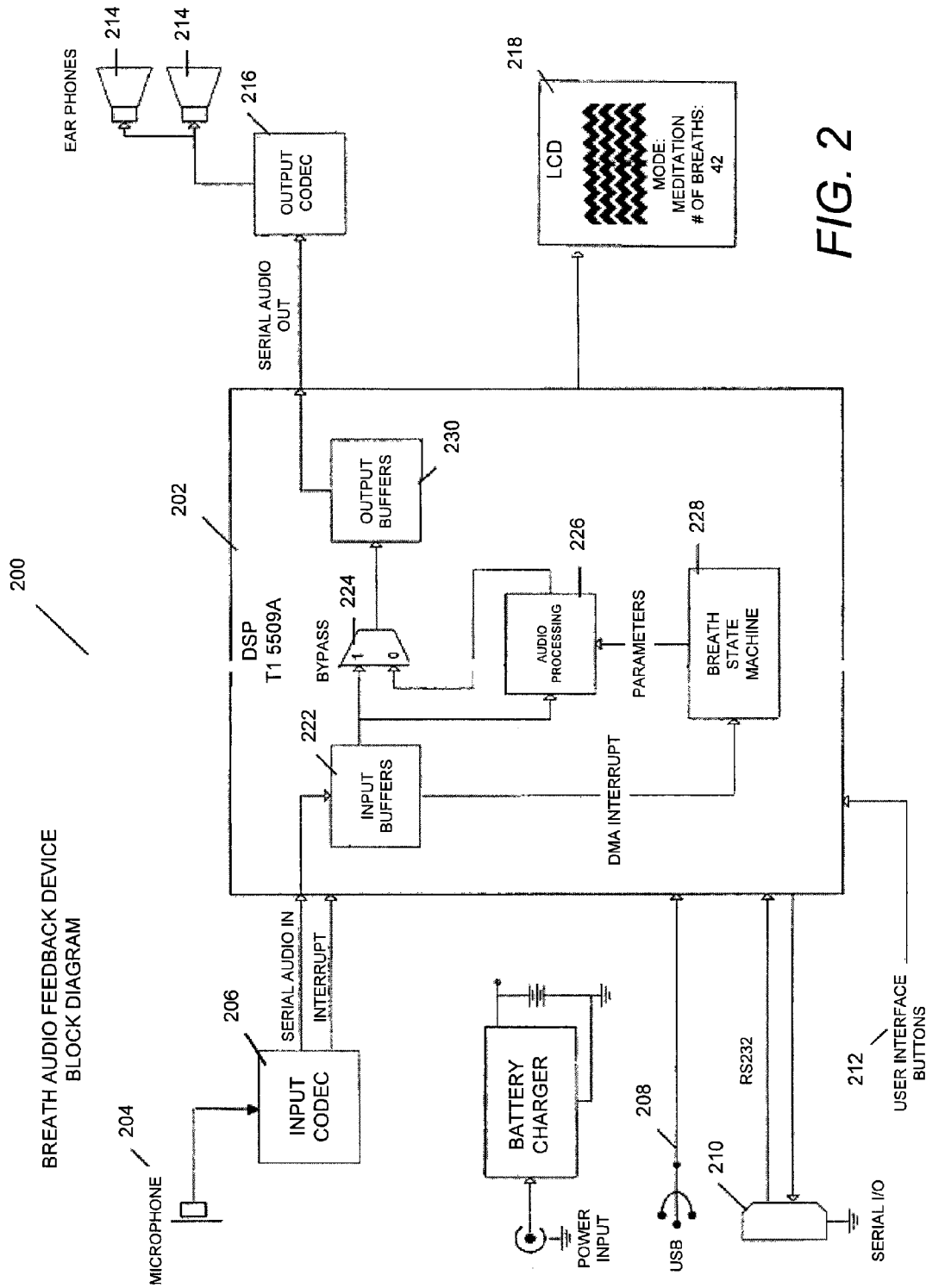
FIG. 2 schematically illustrates a breathing biofeedback device in accordance with many embodiments.

FIG. 2 shows an exemplary block diagram 200 of another embodiment of the breathing biofeedback device in accordance with the present invention. The embodiment of the device shown in FIG. 2, includes a Digital Signal Processor (DSP) 202 that performs the control functions for the device. A microphone 204 is operatively connected with the controller 202 via an input CODEC 206. The input CODEC 206 provides audio input and interrupt signal to the controller 202. The processor 202 can also exchange I/O via a USB 208 and/or a RS232 serial port 210. The controller 202 can also include user interface buttons 212. The controller 202 receives the various input signals, processes them and provides output audio signals to the ear phones via the output CODEC 216. The controller 202 also provides various output signals for display on the display unit 218, which in one embodiment can be an LCD display.

The controller 202 can be a TI 5509A DSP. The controller 202 has an input buffer 222. Input buffer 222 receives input from the audio in and communicates with bypass 224, audio processing 226 and the breath state machine 228. Output from the breath state machine 228, audio processing 226 and the bypass 224 are fed to the output buffers, the earphones 214 and the display device 218.

As described above, the device can be a self-contained, wearable device that provides real-time, interactive, audio biofeedback of the breath. One purpose of this device is to regulate and modify breath patterns, and to support the learning and execution of breathing exercises. It is known that breath patterns contribute significantly to health and illness. Breath awareness and breathing exercises are used in the medical field, the psychological field, and for general health and well being. Breathing exercises are very beneficial, but they can be difficult to learn and execute correctly. The device in accordance with the embodiments of the present invention makes the breath audible to the user in real time. By hearing the breath, neurological connections are made that support breath regulation. Hearing the breath provides more sensory input which makes breathing exercises easier to learn and execute.

In one embodiment, the device in accordance with the embodiments of the present invention can use digital signal audio processing and a Breath State Machine to detect each breath and make the necessary adjustments to provide clean and consistent audio feedback. In addition, the present device can also include specialized modes for different applications, and an effects processor to enhance the sound quality of the breath. Further details of the device and its sub parts are described below.

In one aspect, the device can be a small battery-powered, rechargeable, or plug-in device with a microphone and stereo ear phones (or headphones) that fit on the user's head in a comfortable manner. The device has onscreen display capability. It can stand on its own or be incorporated into mobile and personal devices, computers, biofeedback, medical and exercise equipment. For example, a mobile device (e.g., an iPod, a personal digital assistant (PDA)) can run an application program to achieve the functions of the presently disclosed device.

Input Device:

The input device can include a single acoustic microphone. The microphone acquires sounds of the users breathing. This microphone can be physically mounted in such a way as to maximize sensitivity to the sounds of breathing (through the mouth and nose) while rejecting unwanted ambient sounds (e.g. to maximize signal to noise ratio). The microphone can be wireless or attached at the other end to a headband. The device uses a microphone sensitive enough to pick up breathing sounds. This can be a surface stethoscope microphone, a condenser microphone, or any other state-of-the-art microphone. The microphone can be positioned in such a way as to maximize sensitivity to breathing sounds while rejecting unwanted ambient sounds. (e.g., maximize signal to noise ratio). The input device can be placed near the mouth, nose, throat, thorax, head or other part.

Output Device:

The output device can include binaural earphones. The earphones are configured to convey the output signal to the user while preventing sound leakage that could cause undesirable acoustic feedback. The earphones can be configured to be comfortable and stay physically in place while the user is sitting, lying, in motion and sleeping. Other head pieces can be available for particular applications. The output device can also be a standalone device (or plugged into a standalone device) configured in accordance with the embodiments.

Display Unit:

The display unit can be a PDA, laptop, or a PC or an equivalent intelligent host device. A software program provides an interface with the headband unit. The display unit can also include a separate speaker(s). In one embodiment, the display unit includes a VGA LCD screen with a DXVU meter or other equivalent meter. The display can show basic setup information, status and menus. The DXVU meter can provide a visual display of frequency response. The DXVU meter is an ActiveX control, which can monitor any audio device configured as a recording source, such a Microphone, CD ROM, etc. and display the monitored audio levels like a standard VU Meter or as an oscilloscope. Other means of display can also be used.

For power, options can include dry-cell batteries and lithium-ion rechargeable batteries. All units include an AC adaptor power supply or other means for recharging batteries.

A Remote Control Unit:

A remote control unit can be used with the device so the user can manually adjust volume, settings, timer, and so on.

The User Interface:

The user interface is configured to receive input and provide operational information to the user. The user interface provides various parameters and functionality, including: an ability to interact with the display (e.g., an LCD display) and pushbuttons, etc. The user interface and the device include features for: an on/off switch; volume level control; mode select buttons and indicators. The mode and their available selections include: snoring/sleep apnea with settings for volume output level—baseline, threshold volume, time interval for response to feedback, pitch—volume ratio/limits, statistical analysis (see below); breath training with settings for volume output level, pitch+/−, special effects, reverb (i.e. stadium preset), frequency manipulation; and a timer having a pleasant alarm. The user interface can also be implemented using a mobile device (e.g., a PDA, an intelligent mobile device such as an iPhone). The user interface can be further configured to function with the remote control unit, for example, using a combination of software and/or hardware.

In one aspect, the user interface of the device offers the user the following controls, namely: an on/off switch; a volume control dial; various menu buttons, and navigation controls. The menu on the user interface can be configured to give the user access to setup options, mode selection and features. The setup functions can include: microphone type; earphone type; breath calibration time and personalized setting option. Mode selection functions can include: basic; stress reduction/relaxation; anti-snoring; and fitness training/cardio. Feature settings can include: effects processor and timer.

The output display of the device as a user interface display provides the user with information gathered by the device while operating in one of its several states. In one embodiment, the states include: breath calibration, duration of breath cycle, volume/frequency averages and peaks, and output volume. This data can be saved to the device's memory; the user can delete the information as needed.

As set forth above, the device in accordance with the embodiments of the present invention can function in one of several modes that include a basic mode; a stress reduction/relaxation mode; an anti-snoring; and a fitness training/cardio. The functionality of each of these modes is described in further detail below.

The Basic mode can be used for all applications of breath regulation and training. In this mode, the user can set the output volume, as well as choose an effects preset (such as reverb).

The Anti-Snore mode can detect the wave frequency and volume of a snore. In this mode, the output volume incrementally increases as the input volume increases, to make the breath audible to the sleeping person. The breath becomes audible (without the person fully waking up) and acts as a cue for the user to breathe more quietly. When the input breathing becomes quieter and more like normal breathing, the audio feedback matches the new softer volume with a softer output volume and returns to Basic mode.

The Stress Reduction/Relaxation mode adds other sounds along with the user's breath such as water sounds, nature sounds, music, or a drone. The addition of these sounds enhances relaxed breathing patterns. In this mode, the user can choose the background sound from pre-programmed options, or the background sound can be made available by tapping into other applications on a mobile device (e.g., a music library).

The Fitness Training or Cardio Mode adds the sound of a pulse along with the user's breath. The pulse acts as a cue for the user to breathe at a certain rate or tempo, supporting cardio programs and heart rate variability training. The user can set rate and volume of the pulse.

Signal Processing:

In one embodiment, the signal processing can be an analog-based processing, having a real-time micro-controller based sampling and control. The micro-controller can process the incoming microphone signal and compute a desired output level based on various algorithms. In one exemplary processing of the audio signal, the microphone signal is first pre-amplified to a voltage level that can be processed by an audio envelope detector circuit. This circuit includes a peak detector with a time constant slightly longer than the lowest audio input frequency expected, in this case approximately 100 Hz. The envelope detector signal is then fed into the analog-to-digital converter input of the micro-controller allowing it to constantly sample the input volume level. The micro-controller then controls the final output volume level fed to the headphones utilizing a digitally controlled variable-gain amplifier. In one embodiment, the final output signal is not modified in any manner from the original input, except in volume.

In addition to controlling the output volume, the micro-controller can measure, track and display various statistical parameters indicating the user's performance improvement or regression over a period of time. The statistical analysis can monitor peak volume, lowest volume and an average volume. For the peak and lowest volumes, parameters such as the length of time at that volume and the number of episodes above a threshold can be tracked.

In addition, the device also includes a playback feature so that a breathing session can be digitally recorded and played back through the display unit's speaker(s).

In another embodiment, the novel breathing biofeedback device uses a DSP to modify and enhance the audio output. The DSP also communicates with the user interface and controls the display. As set forth above and shown in FIG. 2, the DSP controller is configured to enable audio processing as well as a breath state machine.

The DSP audio processing can modify the audio buffers by gain control, equalization, frequency shifts and effects processing. The audio processor can clip the output volume. Since different frequencies have different perceived volumes, the different frequency bands can be clipped independently.

Figure 3:
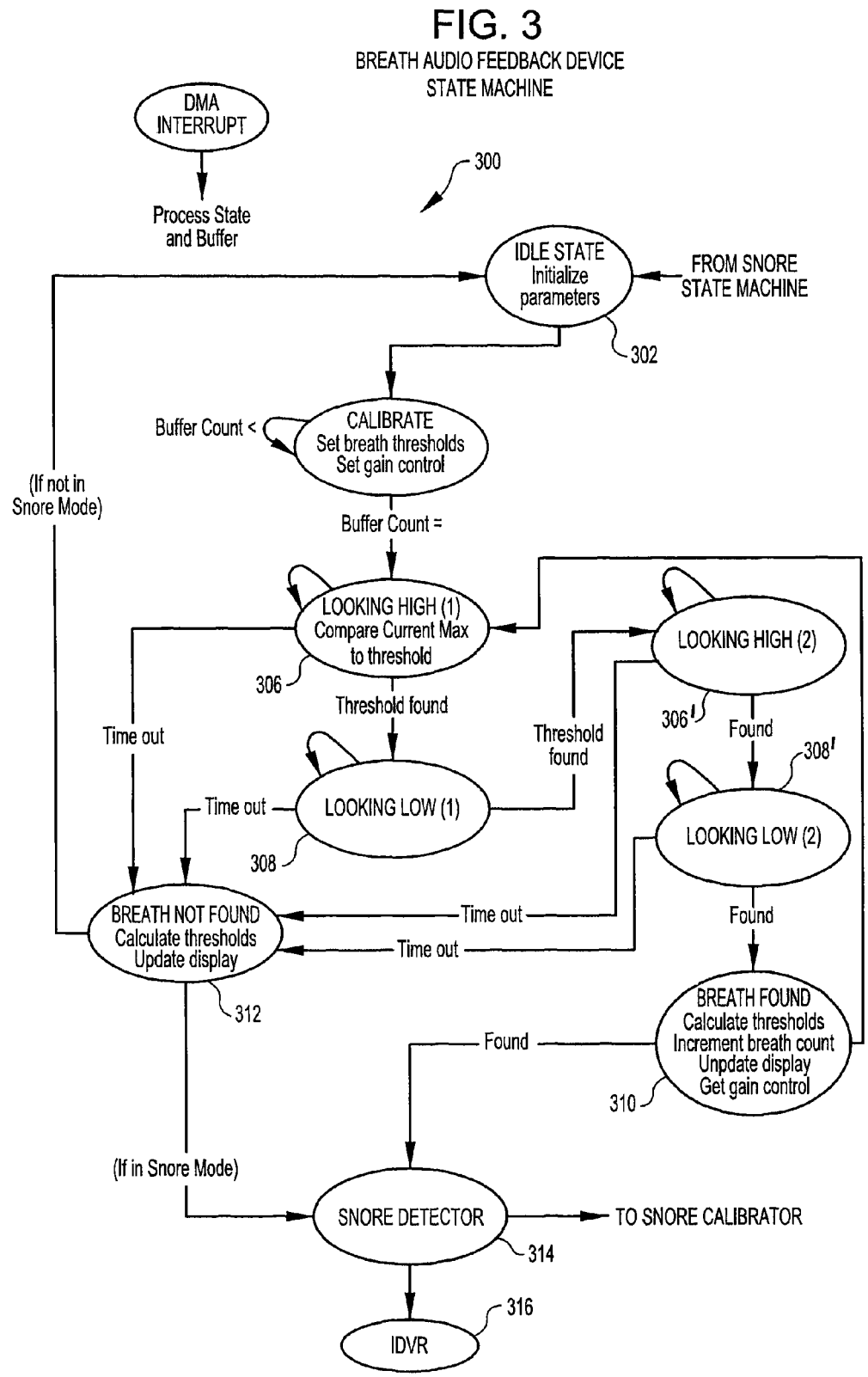
FIG. 3 schematically illustrates functional aspects of a breath state machine of the breathing biofeedback device of FIG. 2.

FIG. 3 shows an exemplary block diagram 300 of one embodiment of the breath state machine. The state machine controls the variables of the audio processor. It first calibrates the device to the incoming breath and then, using the data from the calibration, counts the incoming breaths and modifies the gain and frequency control variables as necessary. The states of the breath state machine are as follows: IDLE 302; CALIBRATE 304; PEAK_DETECT (or looking high) 306; TROUGH_DETECT (or looking low) 308; BREATH_FOUND 310 and BREATH_NOT_FOUND 312. Each of these states is described in further detail below.

The IDLE state resets some state parameters. The CALIBRATE state Loops for some time (e.g., 10 seconds) while keeping track of min and max buffer averages. At the end of the calibration time this information is used to calculate the low and high thresholds for the breath detection states. It also resets the gain control variable.

The Breath Detection States can include four breath detection states, that include PEAK_DETECT, TROUGH_DETECT, PEAK_DETECT2, TROUGH_DETECT2. These four states are used to detect the breath itself. This can be done by taking the average of each buffer as it comes in and comparing it to the thresholds established in the 'Calibrate' state. One breath cycle, which includes inhalation and exhalation, has two high peaks and two low troughs. After two peaks and two troughs have been detected the 'BREATH_FOUND' state is entered. If the threshold is not reached within the timeout period the 'BREATH_NOT_FOUND' state is entered.

The BREATH_FOUND state can be configured to recalculate the thresholds, increments the breath counter, update the display, set the gain control, and modify the equalizer parameters (as necessary). After this state the breath detection state returns to PEAK_DETECT for the next breath cycle.

The BREATH_NOT_FOUND state: When no breath is found the device recalibrates itself. The state machine returns to IDLE, where it resets, and the whole process is started again.

A variation of this state machine can be used in an Anti-Snore mode, enabling the device to detect snores and modify the equalizer and gain controls as necessary. The breath state machine can automatically detect a snore and enter snore mode, when the Anti-Snore mode (Snore detector 314) is enabled. When snoring stops, the state machine automatically reverts to the Basic 402 mode or the non Anti-Snore mode. From the snore mode, an integrated digital voice recorder 316 is used to record the breathing sounds.

Figure 4:
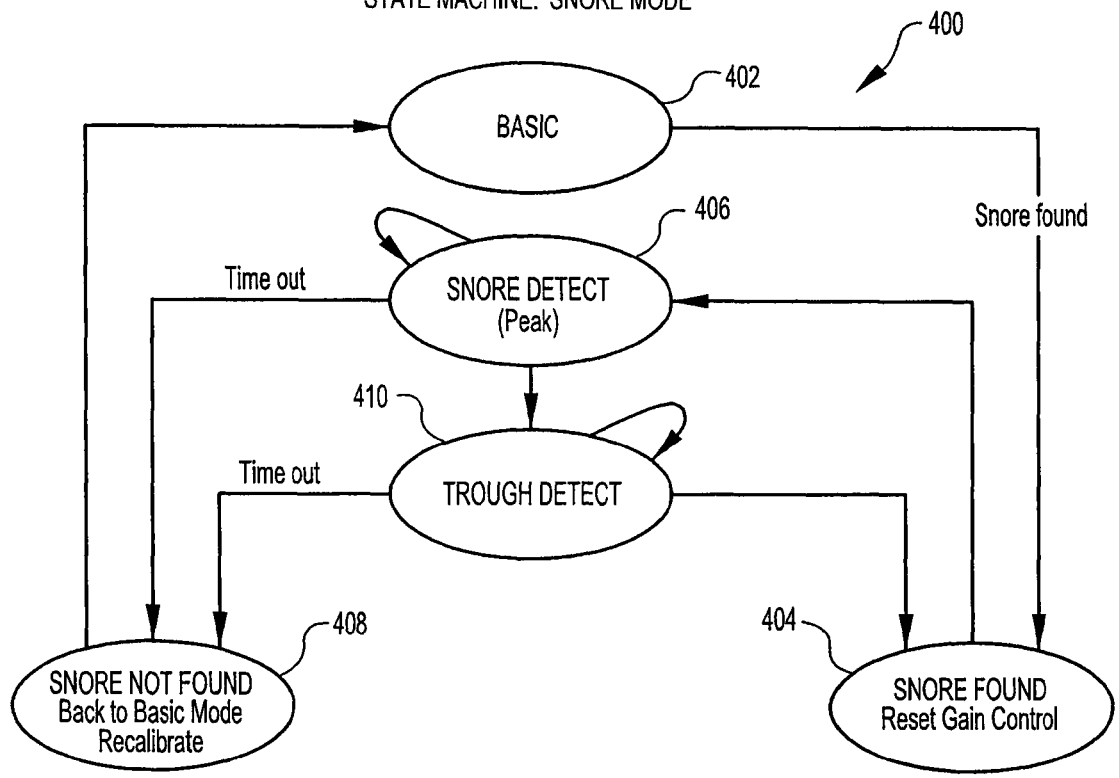
FIG. 4 schematically illustrates snore mode functional aspects of the breath state machine of the breathing biofeedback device of FIG. 2.

FIG. 4 shows an exemplary block diagram 400 of one embodiment of the snore mode of the breath state machine. As shown in FIG. 4, the snore mode can start in the basic mode 402. From the basic mode, once a snore is found or sensed 404, the gain control is reset. Control moves to snore detect to detect the peak volume and/or frequency of the snore sound. This continues until a peak is detected. If a peak is not detected, the process times out and the state reverts to the "snore not found" state 408 and then back to the basic mode 402. When a peak for a snore is detected, then a low point volume and/or frequency is searched for 410. When a trough is found, control is passed to the snore found state 404. When a trough is not found after a period of time, the process times out and the state reverts to the "snore not found" state 408 and then back to the basic mode 402. As described above, the Anti-Snore mode can detect the wave frequency and volume of a snore. In this mode, the output volume incrementally increases as the input volume increases, to make the breath audible to the sleeping person. The breath becomes audible (without the person fully waking up) and acts as a cue for the user to breathe more quietly. When the input breathing becomes quieter and more like normal breathing, the audio feedback matches the new softer volume with a softer output volume and returns to Basic mode. The functionality of the breath state machine can be provided via software run on a suitable device such as a mobile device (e.g., a PDA, an iPhone, or other similar mobile unit).

Respiratory Biofeedback Systems

Over the last 20 years, there has also been extensive research about learning. This research has been motivated, at least in part, by autistic disorders and ADD, academic performance in schools, and an ongoing interest in health and peak performance. Research has revealed that people have specific sensory learning preferences: visual, audio, and kinesthetic. Kinesthetic learning has both sensory (sensing) and motor (movement or doing) functions. It has been shown that a person, who may have difficulty learning using one sense, may have success using another sense. There is also research showing that using more than one sense can dramatically improve learning and performance.

Biofeedback methodologies and technologies can use visual feedback of physiological processes. There is recent evidence that the auditory brainstem is also involved with learning and memory. Being able to listen to our physiological processes may greatly increase conscious and subconscious control of our physiological processes, cognitive learning, and training of our physiological processes. Therefore, in many embodiments of the present invention, a biofeedback methodology is provided that integrates audio, visual, kinesthetic sensory and kinesthetic motor modalities.

Most physiological processes are carried out through involuntary reflexes. Respiration provides a bridge between involuntary and voluntary reflexes, and can be consciously controlled. Respiration is connected to every physiological process in the body. The breathing process can affect, and be affected by all other physiological processes.

Audio feedback of the sound of a person's respiration to the person may result in improved functionality of conscious and subconscious physiological activities. To accelerate the physiological learning and biofeedback processes involved, the sound of the person's respiration can be acquired, modified to accentuate one or more aspects of the respiration sound, and fed back to the person in audio form. The feedback can be supplemented with additional output forms, for example, visual and/or kinesthetic output forms.

Figure 5:
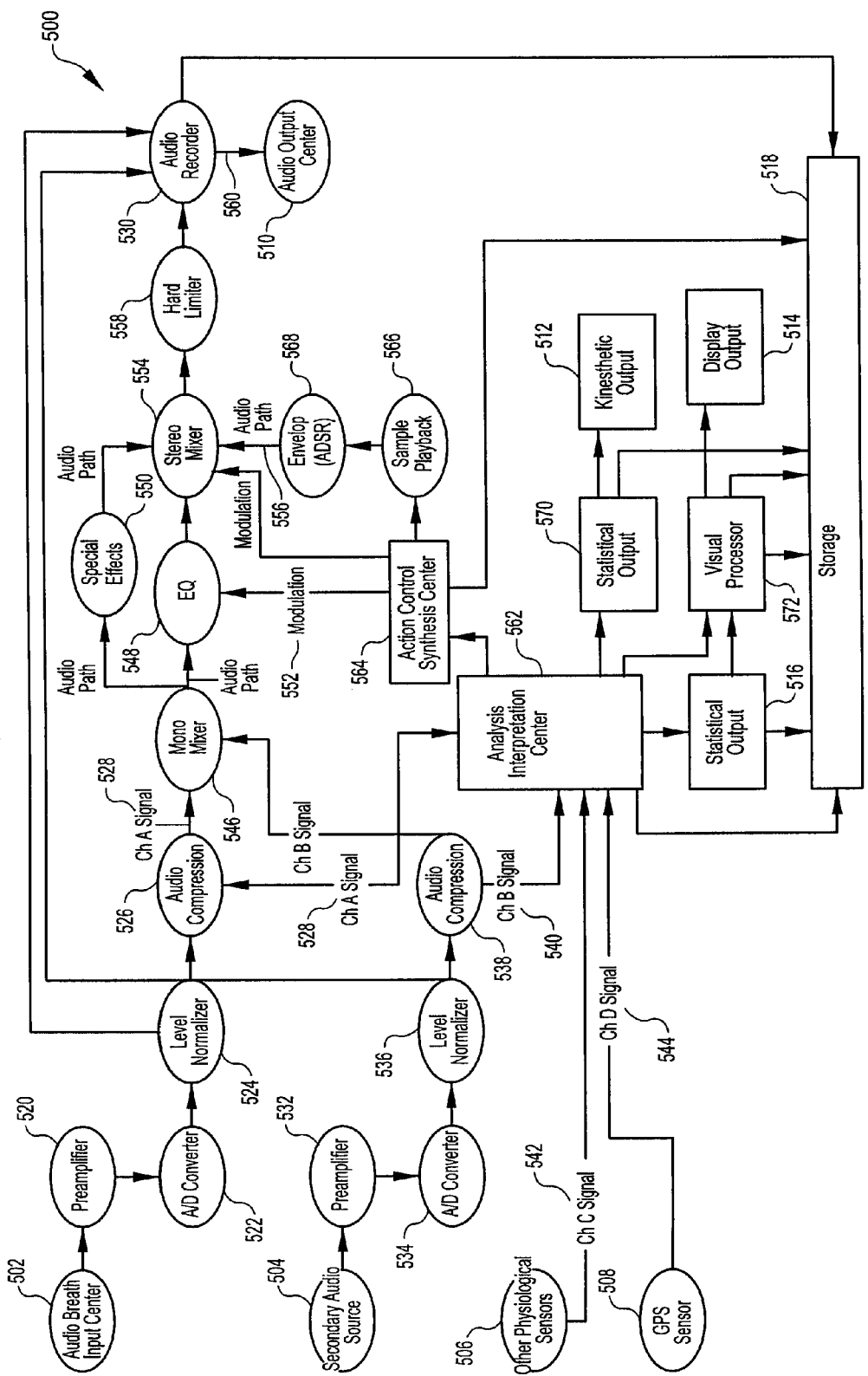
FIG. 5 schematically illustrates a biofeedback system in accordance with many embodiments.

FIG. 5 schematically illustrates a biofeedback system 500 in accordance with many embodiments. The biofeedback system 500 includes a number of input sources, specifically, an audio breath input center 502, a secondary audio source 504, other physiological sensor(s) 506, and a global positioning satellite (GPS) sensor 508. The biofeedback system 500 generates an audio output output to a user via the audio output center 510, a kinesthetic output 512, a display output 514, and statistical output 516. Data corresponding to the statistical output 516, the audio output, the kinesthetic output 512, and/or the display output 514 can be stored in a storage 518 (e.g., an electronic digital memory device). Additional components (described below) process the input received from the input sources to generate the various outputs. One or more of the aforementioned components can be omitted or varied without deviating from the spirit and scope of the invention. The biofeedback system 500 is operable to generate a respiratory signal in response to a user's respiratory activity; process, analyze, and modify the respiratory signal to generate an audio output signal, and convert the audio output signal into sound waves that are output to the user via the audio output center 510.

In many embodiments, the audio breath input center 502 converts sound of the user's respiratory activity into an electrical signal. The audio breath input center 502 can include one or more sensors that generate an electrical signal in response to sensing the user's respiratory activity. The one or more sensors can include, for example, a microphone and/or a transducer. The one or more sensors are not limited to sensors that convert audible respiratory sounds, but can include any sensor that indirectly measures respiratory activity, for example, a respiratory monitor, an air flow monitor, a vibration monitor, or other sensors that generate an output signal correlated with respiration. The signal from the audio breath input center 502 can be amplified by a preamplifier 520. An analog to digital (A/D) converter 522 can receive the output from the preamplifier 520 and can convert the output into a digital signal. The digital signal from the A/D convert 522 can be processed by a level normalizer 524. The output from the level normalizer 524 can be then subjected to audio compression 526 so as to generate a channel A (Ch. A) signal 528. The output from the level normalizer 524 can also be supplied to an audio recorder 530.

The secondary audio source 504 generates an audio signal that can be processed, analyzed, modified, and/or added to the audio output signal. For example, the secondary audio source 504 can be used by a coach or teacher to give verbal instructions that are output to the user. The secondary audio source 504 generates a signal that can be amplified by a preamplifier 532. An analog to digital (A/D) converter 534 receives the output from the preamplifier 532 and converts the output into a digital signal. The digital signal from the A/D converter 534 can be processed by a level normalizer 536. The output from the level normalizer 536 can be then subjected to audio compression 538 so as to generate a channel B (Ch. B) signal 540. The output from the level normalizer 536 can also be supplied to the audio recorder 530.

The other physiological sensor(s) 506 can include, for example, a heart sensor(s), a brainwave sensor(s), a temperature sensor (s), a muscle tension sensor(s), an arterial pressure sensor(s), an oxygen sensor(s), a glucose sensor(s), a medical imaging device(s), a blood oxygen saturation sensor(s), and/or any other physiological sensor. The other physiological sensor(s) 506 generate a channel C (Ch. C) signal 542 in response to an electrical signal, a pressure variation, a gas(es), a temperature(s), a chemical(s), and any other physiological activity based stimulus from outside or inside the user's body. The Ch. C signal 542 can be integrated and correlated with the Ch. A signal 528 and/or the Ch. B. signal 540.

For example, heart rate variability is intimately connected with respiration. In a healthy person, the heart rate goes up during inhalation, and the heart rate goes down during exhalation (respiratory sinus arrhythmia). Accordingly, analysis and interpretation of the Ch. A signal 528 can be integrated with analysis and interpretation of the Ch. C signal 542 from a heart sensor. The correlated signals enable the measurement and/or formulation of correlations between respiratory patterns and heart activity patterns. In many embodiments, a user can listen to a respiratory based audio output while observing their heart activity. Such respiration and heart activity feedback can help the user to attain heart health, well-being, and/or peak performance. For example, the respiratory feedback and the heart activity feedback, coupled with analysis and interpretation of the user's respiratory activity and/or heart rate, can improve a patient's success with heart rate variability protocols and goals. The audio breath experience and/or generative sounds, music and art based on patterns acquired from the user's breath, and/or patterns of optimal breathing can re-enforce desired heart activity. In many embodiments, the user can be presented with information regarding heart health (e.g., heart rate variability) during the respiratory feedback, which can help to improve the user's respiratory patterns.

When the other physiological sensor(s) 506 includes one or more brainwave sensors, the signal(s) generated by the brainwave sensor(s) can be analyzed in conjunction with the corresponding respiratory signal(s). The correlated signals and/or data enable the measurement and/or formulation of correlations between respiration patterns and brainwave patterns. The brainwave signal(s), analysis, and/or interpretation of the brain wave signal(s) can be fed back to the user along with the respiratory based feedback. The combined feedback enables the user to learn to regulate the user's brainwave pattern(s) by regulating their respiratory pattern(s). For example, listening to a respiratory based feedback enables the user to achieve increased self-awareness, which can result in increased desirable alpha activity. The combined data, feedback, and/or synthesis also enables the user to reinforce desired brainwave states.

When the other physiological sensor(s) 506 includes a glucose sensor, the signal generated by the glucose sensor can be analyzed in conjunction with the corresponding respiratory signal(s). The correlated signals and/or data enable the measurement and/or formulation of correlations between respiration patterns and glucose levels. The glucose signal, data, analysis, and/or interpretation of the glucose signal can be fed back to the user along with the respiratory based feedback. The combined feedback enables the user to learn to regulate the user's glucose level by regulating their respiratory pattern(s).

The other physiological sensor(s) 506 can include audio physiological sensors. For example, an audio sensor can be used to generate an input signal in response to sound from the user's heart. In many embodiments, the heart sound based input signal is used to generate an audio signal that is added into the audio output signal so that sound based on both the user's respiratory activity and the user's heart activity are output to the user. The user can listen to both audio signals, as well as receive analysis and other sensory feedback to attain optimal health and performance. Other physiological sounds can also be used to generate audio output for output to the user. This ability is quite useful and medically proven as a meditation aid. For example, audio output can be generated from sounds of the user's nervous system, cellular activity, organs, or any other physiological activity that can be used to generate an audio output signal. The such audio output can be output to the user alone and in any combination thereof. Audio signals of physiological phenomena can also be interpreted and fed back to the user via sound synthesis. Recorded sounds and/or synthesized sounds can be used to generate the sound that is output to the user, and the sound can be enhanced to improve health, for artistic purposes, for musical purposes, and the like.

The GPS sensor 508 can be used to track the location, speed, direction and/or distance traveled by the user. The GPS sensor 508 generates a channel D (Ch. D) signal 544 that can be processed with the Ch. A signal 528, the Ch. B. signal 540, and/or the Ch. C signal 542. One or more other location related sensors can be used in place of the GPS sensor 508, for example, a gyroscope, a compass, one or more accelerometers, and/or a hand held intelligent host device that includes a location related sensor, such as a PDA, an iPhone, etc. The information generated by the GPS sensor 508 can be integrated into the analysis, interpretation and multi-sensory feedback of the audio respiratory signal. For example, one or more users can track his or her breath patterns in reference to location, speed, direction and/or distance.

The Ch. A signal 528 forms the basis for an audio signal that can be modified and output to the user. A mono mixer 546 can be used to combine the Ch. B signal 540 with the Ch. A signal 528. The output from the mono mixer 546 can be input into an equalizer (EQ) 548, and can also be subjected to special effects 550. The equalizer 548 can receive a control input (modulation 552) to control the settings of the equalizer 548. A stereo mixer 554 receives the output from the equalizer 548, the special effects 550, and another audio path 556 (described below). The output from the stereo mixer 554 can input into a hard limiter 558, which limits the volume level of the sound output to the user so as to avoid subjecting the user to sound of an excessive volume level. The output from the hard limiter 558 can input into the audio recorder 530, and the output from the audio recorder 530 is input into the audio output center 510, which outputs an audio output signal 560 received from the audio recorder 530 to the user.

The audio output center 510 can be anything that produces a sound. The audio output center 510 can include more than one audio output. For example, there can be earphones, speakers, and/or any other sound producing technology for outputing sound to one or more users.

The audio recorder 530 provides the ability to record a feedback session, pause a feedback session, stop a feedback session, and play a feedback session back. The audio recorder 530 can be used to record raw respiratory sounds via the input from the level normalizer 524 associated with the Ch. A signal 528, record the secondary audio via the input from the level normalizer 536 associated with the Ch. B signal 540, record the audio signal from the hard limiter 558, and/or record the audio output signal 560.

Control over the audio output signal output to the user is provided by an analysis interpretation center 562 and an action control synthesis center 564. The analysis interpretation center 562 receives separate local or remote components such as the Ch. A signal 528, the Ch. B signal 540, the Ch. C signal 542, and the Ch. D signal 544 as inputs. In many embodiments, the analysis interpretation center 562 analyzes and interprets the Ch. A signal 528, the Ch. B signal 540, the Ch. C signal 542, and/or the Ch. D signal 544, and provides results from the analysis/interpretation as input to the action control synthesis center 564. The action control synthesis center 564 uses the analysis/interpretation results received from the analysis interpretation center 562 to control the equalizer 548, the stereo mixer 554, and/or generate synthesized sounds that are supplied to the stereo mixer 554. Although the analysis interpretation center 562 and the action control synthesis center 564 are illustrated as separate, the functions of the analysis interpretation center 562 and the action control synthesis center 564 can be provided by one, two, or any appropriate number of separate components. For example, a single processing unit comprising a processor and tangible medium comprising control instructions for the processor can be used to provide the functions of the analysis interpretation center 562 and the action control synthesis center 564.

In many embodiments, the Ch. A signal 528 is processed and interpreted by the analysis interpretation center 562 to quantify sound levels of the user's respiratory activity. The determined sound levels can be used by the action control synthesis center 564 to cause the equalizer 548 and/or the stereo mixer 554 to modify the audio signal (e.g., the Ch. A signal 528, the combined Ch. A signal 528 and Ch. B signal 540) to magnify portions of the audio signal corresponding to portions of the Ch. A. signal 528 with sound levels exceeding a desired sound level.

The analysis interpretation center 562 contains algorithms can be configured to analyze and interpret the Ch. A signal 528 and/or the Ch. C signal 542 in a variety of ways. The algorithms can be filter based as well as contain support vector machines that can learn to recognize breath characteristics and patterns. For example, the analysis/interpretation can include Fast Fourier Transform (FFT) based analysis; measurement, processing, and/or transformation of amplitude, duration, sound level (dB), sound frequency (Hz), beats, silences, attack, decay, sustain, release, and other audio phenomena and patterns. Further interpretation can include measurement and/or analysis of respiratory aspects, for example, phases of respiration, a respiration cycle, and/or respiration cycles. Phases of respiration can include inhalation, inhalation transition, exhalation, exhalation rest, and the like. Further interpretation and/or analysis can include determination of respiratory rates and parameters; identification of shallow breathing, deep breathing, optimal breathing, anxious breathing, meditative breathing, yogic breathing, snoring, and/or apnea; assessment of performance breathing for activities; and/or any other interpretation and/or analysis of aspects of breathing.

The action control synthesis center 564 is operable to generate a synthesized representation, for example, in response to input from the analysis interpretation center 562. A synthesized representation can include sound enhancements. For example, a synthesized representation based on the Ch. A signal 528 can include an equalizer adjustment, an amplification, reverb, other sound enhancing audio processing, and/or the like. The action control synthesis center 564 can bring out certain characteristics in the Ch. A signal 528 while subduing other characteristics in the Ch. A signal 528. The action control synthesis center 564 can generate a sound with characteristics of the Ch. A signal 528 using, for example, psychoacoustics to create an audio representation of the user's respiratory activity that can be dimensional, meaningful, therapeutic, pleasant, realistic, and/or the like. Psychoacoustics, the subjective experience of sound, can be used. For example, to the human ear, lower frequencies tend to sound softer and higher frequencies tend to sound louder. Audio characteristics of the respiratory signal can be modified based on how the listener may perceive them, and for creative and therapeutic purposes. The action control synthesis center 564 can use an algorithm to process the respiratory signal to generate sound that mirrors aspects of the user's breath rhythm, intensity, and the like.

The action control synthesis center 564 can have thresholds and also be used to generate an audio cue(s) output to the user. An audio cue(s) can include audio processing of the synthesized representation and/or an additional sound track. For example, an audio cue(s) can be triggered or chosen to accentuate any phase of the user's respiration, a respiration cycle as a whole, and more than one respiration cycle over time. Audio processing can accentuate any part of the user's respiration. The audio cue(s) can include additional tracks such as music, sounds, respiration recordings, verbal instruction, and/or any other audio phenomena. There can be audio templates from which to select the audio cue(s). The audio templates can include composed and/or created sounds and/or music. For example, music, sound, and verbal instructions can support desired outcomes. Ambient sounds and talking can be an additional sound track to train the user to maintain focus and quell negative self talk. The audio templates can also include existing audio sources using any suitable network or technology. For example, the action control synthesis center 564 can supply an input to a sample playback component 566 that triggers the transmission of an audio signal from the sample playback component 566. The audio signal transmitted from the sample playback component 566 can include a recordings of an earlier feedback session made by the audio recorder 530. The recording of the earlier feedback session can be played on its own or as an additional track during a new live breathing feedback session. The recording of the earlier feedback session can also be output from a separate local or remote device using a wired or wireless connection.

An envelope control setting(s) can be used to shape the audio cue(s). These settings can include, for example, attack, decay, sustain, release and other audio processing settings. For example, the envelope control setting(s) can be implemented by an attack-decay-sustain-release (ADSR) envelope 568 to modulate some aspect (e.g., volume) of the audio signal transmitted from the sample playback component 566. The output from the ADSR envelope 568 can input into the stereo mixer 554 for combination with the input from the equalizer 548 and/or the special effects 550.

A kinesthetic processor 570 receives input from the analysis interpretation center 562. The input received can include analysis and/or interpretation results from the analysis interpretation center 562, and can include raw or modified versions of the Ch. A signal 528, the Ch. B signal 540, and/or the Ch. C signal 542. The kinesthetic processor 570, in conjunction with the kinesthetic output 512 generate kinesthetic representations of one or more audio breath inputs, and other physiological inputs or haptic inputs. For example, the kinesthetic representations can include vibrations, touch, movement, or any other kinesthetic phenomena. In another example, a kinesthetic representation(s) can be triggered or chosen to accentuate any phase of the breath, the breath cycle as a whole, and more than one breath, and any other accompanying physiological or audio/visual data.

There can be prompts for haptic inputs. One can touch a key on a keyboard or phone, touch an area on a device that has touch sensors, and/or move or reorient the device as might be detected by an accelerometer or other sensor(s). Haptic inputs can be at the onset, during or conclusion of any breath phase, and/or one or more breath cycles. This can aid the algorithm in the detection of the respiratory signal. Haptic inputs evoke movement and touch as an additional feedback modality for learning, regulation and performance. Prompts for haptic inputs can happen during the entire respiratory cycle(s) and session and increase with added complexity. Haptic inputs can also utilize buttons and joysticks.

The kinesthetic output 512 can be any kinesthetic medium, movement, vibration or haptic output. For example, computers, mobile devices, watches, jewelry, pens, robotic devices, stuffed animals, models, and/or the like, can be used to output a kinesthetic representation of a physiological phenomena. In another example, breathing exercises can include the goal of controlling an animatronic toy animal or toy vehicle (or computer representation of the same). For example, any suitable object can move, vibrate, etc. in response to the respiratory signal. An anatomical model can move three dimensionally in response to the respiratory signal. The sequential activity of the muscles involved with each phase of the breath can move in response to the respiratory signal. The bones of the ribcage and the organs, and all the systems of the body can move in response to the respiratory signal(s), and/or other physiological signals. A stuffed animal can have gestures or full body movements in response to the respiratory signal(s). For example, an animatronic toy or vehicle can accelerate, spin, jump, decelerate, pause, etc. Watches, jewelry, pens, etc can contain LED or a digital medium that can display visual representations in response to the respiratory signal. They can also contain temperature mediums to become warmer or cooler in response to the respiratory signal. All of the above can be recorded and played back.

A visual processor 572 receives input from the analysis interpretation center 562. The input received can include analysis and/or interpretation results from the analysis interpretation center 562, and can include raw or modified versions of the Ch. A signal 528, the Ch. B signal 540, and/or the Ch. C signal 542. The visual processor 572 can create a visual representation(s) of one or more audio breath inputs, another accompanying physiological input(s), and any additional audio track(s). The visual processor 572 can generate, for example, color images, lighting, graphic and animated visualizations, particle displays, and/or generative art based on the patterns inherent in the audio signal of the breath. A three-dimensional particle generator can input graphic or audio representations in multi-dimensions, as is understood in the art. The visual processor 572 can generate graphic, photographic, film, animation, and holographic representations in multi-dimensions. The generated representations can include two dimensional, three dimensional, and/or any suitable visual technology. The visual processor 572 can generate the representations using visual templates. The visual templates can be created and/or from an existing visual source. The visual processor 572 can generate the representations while the user is listening to the audio output by the audio output center 530. The generated visual representations can be viewed by the user while the user listens to the audio output, and/or can be recorded for subsequent play back. The functionality of the visual processor 572 can be implemented via a software application running on an appropriate device such as an intelligent handheld device (e.g., a PDA, an iPhone, etc.).

The display output 514 receives and displays the visual representations generated by the visual processor 572. The display output 514 can be any visual display device, for example, a video monitor, a computer monitor, a mobile phone display, a mobile device display, a television, a projector, and/or any other suitable display device. For example, a visual representation(s) of all or part of one or more audio breath signals can be seen on the walls or ceiling of a room, and/or can be seen on a suitable handheld device. The display output 514 can be capable of showing any type of visual representation generated by the visual processor 572.

The analysis interpretation center 562 generates the statistical output 516 from the Ch. A signal 528, the Ch. C signal 542, and/or the Ch. D signal 544. The statistical output 516 can be for one or more persons, locations, timelines, and/or groups. For example, there can be statistical data of breathing patterns of a group or groups at any same or different location and/or time. The statistical output 516 can include average, minimum values, or maximum values over varying periods of time. The statistical output 516 can be used to provide comparisons with an individual's past performance or that of other groups or norms, over time and/or in different situations. The statistical output 516 can be supplied to the visual processor 572 to generate a visual representation(s) to display the statistical output 516 textually and/or graphically. The statistical output 516 can also be used to control the responsiveness, target values, and/or other settings of the system itself.

The storage 518 can be used to store data received from the analysis interpretation center 562, the visual processor 572, the kinesthetic processor 570, the action control synthesis center 564, and/or the audio recorder 530. The storage 518 can also store the statistical output 516 generated by the analysis interpretation center 562. The storage 518 can be used to store all data that has been received so that it can be retrieved at any time. For example, the storage 518 can include a database capable of managing and/or storing audio, visual, kinesthetic, written and verbal data. The storage 518 can be accessed via a website, and/or can be a server, a storage disk, a memory chip, an optical storage media, and/or any other storage medium and/or technology. For example, when the device operates as a configured handheld device, the storage 518 can be local and/or any local or remotely accessible storage (e.g., a server).

In many embodiments, parts or all of a respiratory-based biofeedback device, system, and/or method can be embodied within any network, technology, system, device, audio, visual and/or kinesthetic medium. For example, such devices, systems, and/or methods can be embodied within a portable, self-contained device, or within a personal device communicating by a wired or wireless means to another local device such as a personal computer or by communications infrastructure such as a phone or data network to a remote web site, network server, or service provider. Recording and communications can either be in real-time or performed off-line, stored, and transmitted later. The various subsystems can be implemented in the personal device or on the associated local or remote devices available to the user. A variety of business models can be employed to provide or give access to the activities or services, including a membership, subscription, one-time or ongoing engagement, or open access to a free or advertising-sponsored service.

Figure 6:
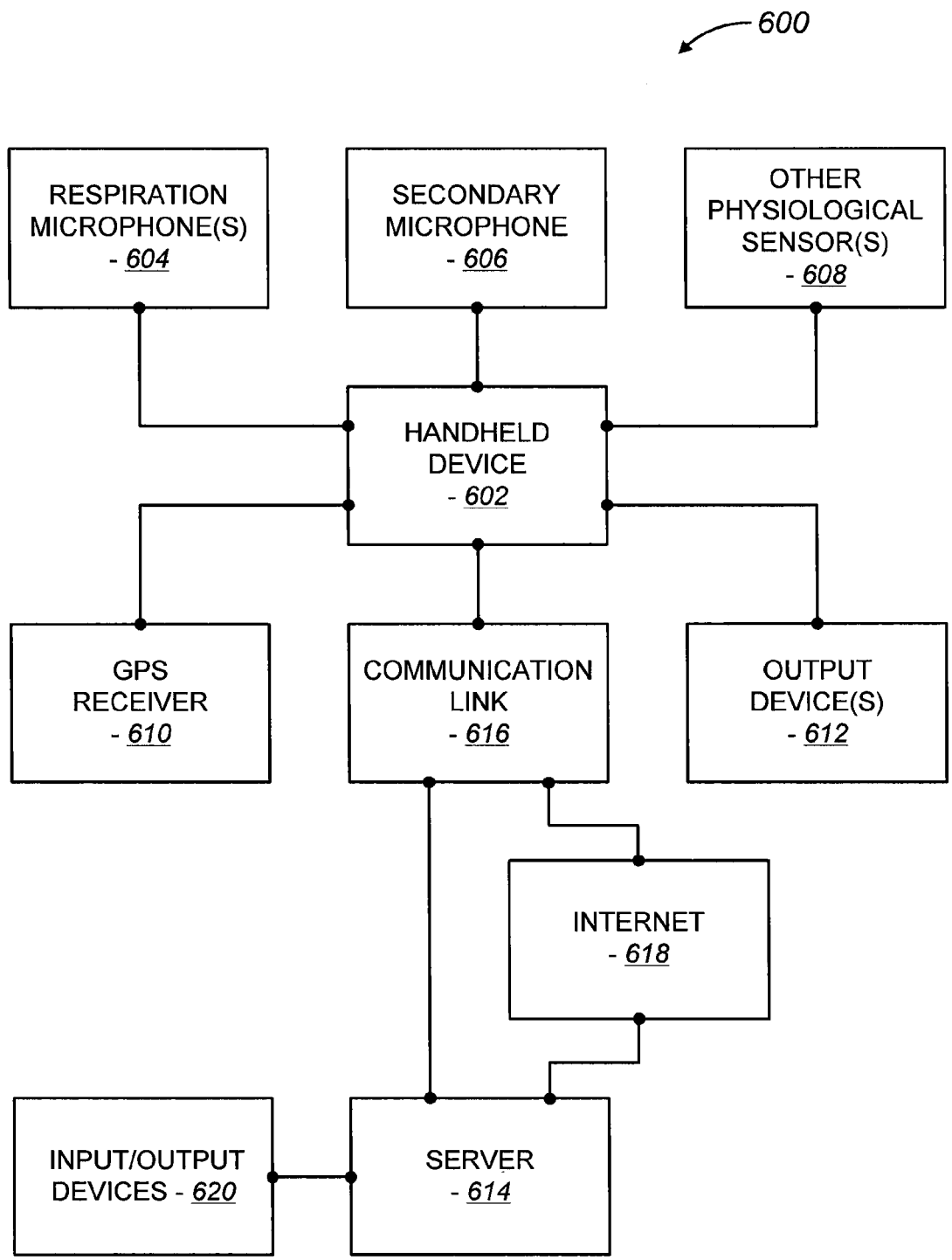
FIG. 6 schematically illustrates a biofeedback system in accordance with many embodiments.

FIG. 6 schematically illustrates a biofeedback system 600 in accordance with many embodiments. The biofeedback system 600 includes a handheld device 602, a respiration microphone(s) 604, a secondary microphone 606, an other physiological sensor(s) 608, a GPS receiver 610, and an output device(s) 612. The handheld device 602 can be communicatively coupled continuously or intermittently with a server 614 via a communication link 616 and/or the internet 618. Input/output devices 620 are communicatively coupled with the server 614, and can be used, for example, by a instructor or coach to communicate instructions to a user of the handheld device 602. The biofeedback system 600 can be configured to provide some or all of the functionality described herein with respect to the biofeedback system 500, and/or described below with respect to the biofeedback method 700.

The respiration microphone(s) 604 converts sound of the user's respiratory activity into a respiratory signal input into the handheld device 602. The respiration microphone(s) 604 can be located in a suitable location to capture sound of the user's respiratory activity, for example, in or near the user's nostrils so that the user can breathe through their nose during the respiratory feedback session, which may be preferable with respect to the goals of a biofeedback session and can serve to enhance the respiratory signal by locating the microphone(s) near an area of relatively high airflow velocity. The handheld device 602 can include suitable circuitry to convert the signal from the respiration microphone(s) 604 into a suitable respiratory signal (e.g., a digital signal, an analogue signal). For example, the handheld device 602 can include circuitry that provides the functionality provided by the preamplifier 520, the analog-to-digital converter 522, the level normalizer 524, and the audio compression 526 described above with reference to the biofeedback system 500 of FIG. 5.

The secondary microphone 606 can be optionally used to generate a secondary audio signal for use during a biofeedback session. For example, the secondary microphone 606 can be used by a coach or instructor to provide instruction to the user during a biofeedback session. The handheld device 602 can include suitable circuitry to convert the signal from the secondary microphone 606 into a secondary audio signal (e.g., a digital signal, an analogue signal). For example, the handheld device 602 can include circuitry that provides the functionality provided by the preamplifier 532, the analog-to-digital converter 534, the level normalizer 536, and the audio compression 538 described above with reference to the biofeedback system 500 of FIG. 5.

The other physiological sensor(s) 608 can be optionally used to generate input signals in response to one or more physiological activities of the user. The other physiological sensor(s) 608 can include any of the sensors described above with reference to the other physiological sensors 506 of FIG. 5, and can be used to provide any of the related functionality described herein.

The GPS receiver 610 can be optionally used to generate location information for the user and input the location information into the handheld device 602. The handheld device 602 can also include an integral GPS receiver for generating location information for the user. Alternative location information generation devices, as described herein, can also be used to generate and input location information into the handheld device 602, and/or can be integrated with the handheld device 602.

The output device(s) 612 can include one or more of any of the output devices described herein. For example, the output device(s) 612 can include an audio output device (e.g., a speaker(s), a headphone, ear buds, and any of the devices discussed above with regard to the audio output center 510 of FIG. 5), which can provide some or all of the functionality discussed previously with regard to the audio output center 510 of FIG. 5. The output device(s) 612 can also include a kinesthetic output (e.g., any of the devices discussed herein with regard to the kinesthetic output 512 of FIG. 5), which can provide some or all of the functionality discussed herein with regard to the kinesthetic output 512 of FIG. 5. The output device(s) 612 can also include a display output (e.g., any of the devices discussed previously with regard to the display output 514 of FIG. 5), which can provide some or all of the functionality discussed herein with regard to the display output 514 of FIG. 5. In many embodiments, the display output is integrated with the handheld device 602.

The handheld device 602 can be a device configured to solely or primarily provide the respiratory-based biofeedback functionality described herein, and can be a multi-purpose device (e.g., a PDA, an intelligent cellular phone, music or video player, etc.) that runs an application that provides the respiratory-based biofeedback functionality described herein. The handheld device 602 can receive input from the respiration microphone 604, the secondary microphone 606, the other physiological sensor(s) 608, and/or the GPS receiver 610, and generates an output(s) for the output device(s) 612. In many embodiments, the handheld device 602 provides the functionality described herein with regard to the biofeedback system 500 of FIG. 5.

In many embodiments, the handheld device 602 can be operated independently of a server 614, and can be operated while in communication with the server 614 via the communication link 616 (e.g., a wireless connection, a wired connection). The communication link 616 can also be used to connect the handheld device 602 to the interne 618 (or other suitable communication network), which provides for continuous or intermittent communication with the server 614. In many embodiments, either or both the handheld device 602 and the server 614 provide data processing and data storage functionality for the biofeedback system 600. For example, the handheld device 602 can be configured to provide real time processing of the input signal(s) to the handheld device 602 to generate output to the output device(s) 612 in real time response to the user's respiratory activity, and the server 614 can be used to store data for one or more users, including themselves. The server can also be used to provide application program updates to the handheld device 602, provide remote processing of data for the one or more users, and/or can be used to provide group based data to the handheld device 602, for example, group based respiratory data that can be used to inform the user of the handheld device 602 regarding how the user's respiratory activity compares to a group of users (e.g., athletes, users of a particular age, and the like).

In many embodiments, the server 614 is coupled with input/output devices 620 (e.g., a display, an audio output, an audio input, a keyboard) by which a person (e.g., a coach, an instructor) can interact with the user of the handheld device 602 via the server 614. For example, such a person can provide instruction as described herein with regard to the secondary audio source 504 of FIG. 5. The input/output devices 620 can also be used to operate and/or maintain the biofeedback system 600.

Respiratory Biofeedback Methods

Figure 7:
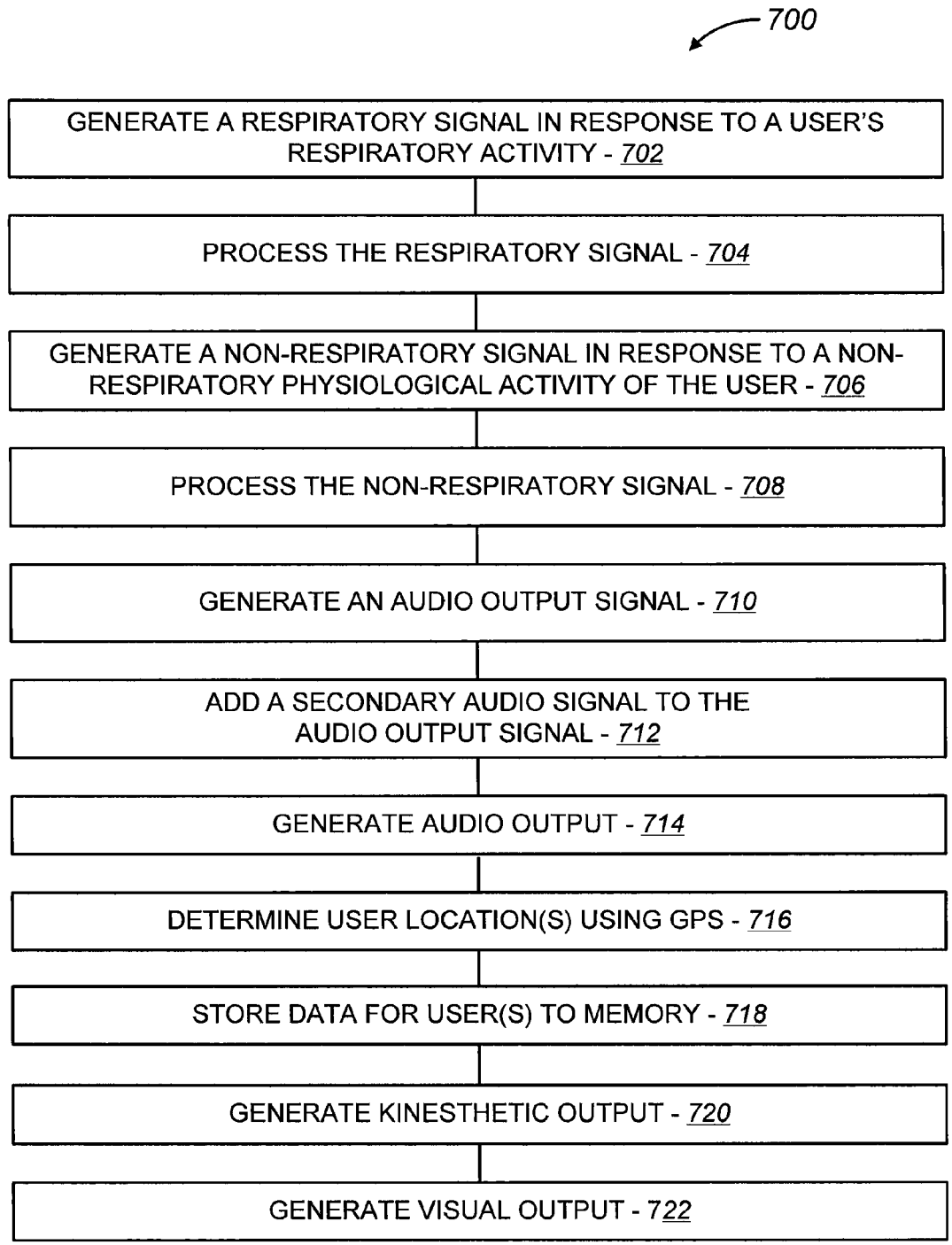
FIG. 7 is a block diagram of a biofeedback method in accordance with many embodiments.

FIG. 7 is a block diagram of a biofeedback method 700 in accordance with many embodiments. The above described biofeedback devices and systems have included many examples and variants which can be configured for use in practicing the method 700.

In step 702, a respiratory signal can be generated in response to a user's respiratory activity. In many embodiments, the respiratory signal can be generated using a microphone to convert the sound of the user's respiratory activity into the respiratory signal. In many embodiments, a deflection based sensor can be used to measure respiration related deflection of the user to generate the respiratory signal.

In step 704, the respiratory signal generated in step 702 is processed. For example, an audio based respiratory signal can be processed to quantify the sound levels of the user's respiratory activity that exceed a specified sound level. Additionally, the analysis/interpretation can include Fast Fourier Transform (FFT) based analysis; measurement, processing, and/or transformation of amplitude, duration, sound level (dB), sound frequency (Hz), beats, silences, attack, decay, sustain, release, and other audio phenomena and patterns. Further interpretation can include measurement and/or analysis of respiratory aspects, for example, phases of respiration, a respiration cycle, and/or respiration cycles. Phases of respiration can include inhalation, inhalation transition, exhalation, exhalation rest, and the like. Further interpretation and/or analysis can include determination of respiratory rates and parameters; identification of shallow breathing, deep breathing, optimal breathing, anxious breathing, meditative breathing, yogic breathing, snoring, and/or apnea; assessment of performance breathing for activities; and/or any other interpretation and/or analysis of aspects of breathing.

In step 706, a non-respiratory signal is generated in response to a non-respiratory physiological activity of the user. For example, one or more of the non-respiratory physiological activities described above with reference to the other physiological sensor(s) 506 of the biofeedback system 500 can be measured so as to generate the non-respiratory signal.

In step 708, the non-respiratory signal generated in step 706 is processed. For example, when the non-respiratory representation concerns the user's heart activity, the heart rate of the user can be determined. As another example, when the non-respiratory activity concerns the user's blood glucose level, the user's blood glucose level can be determined.

In step 710, the respiratory signal generated in step 702 is modified to generate an audio output signal. In many embodiments, the respiratory signal is modified in response to one or more quantified aspects of the respiratory signal itself. For example, the respiratory signal can be used to generate an audio output signal that includes the respiratory signal modified to accentuate a portion of the respiratory signal having an intensity level above a specified intensity level. In many embodiments, the generated audio output signal includes the respiratory signal modified to increase a volume level of a portion of the respiratory signal where the volume level exceeds a specified volume level. In many embodiments, the generated audio signal includes the respiratory signal modified in response to one or more quantified aspects of the non-respiratory signal. For example, the respiratory signal can be modified in response to the heart rate of the user.

In step 712, a secondary audio signal is added to the audio output signal. For example, a secondary audio signal can include instructions from a coach or instructor to be output to the user during a respiratory biofeedback session.

In step 714, audio output is generated from the audio output signal. In many embodiments, the audio output signal is converted into sound waves output to the user.

In step 716, one or more locations for the user are determined using a global positioning satellite (GPS) system receiver, or other location-sensing mechanism. The determine locations can be used to determine other location related information for the user (e.g., speed(s), distance(s) traveled).

In step 718, data for the user(s) is stored in memory. The stored data can include any information processed during the accomplishment of the method 700. For example, the stored data can include the respiratory signal, data derived from the respiratory signal, the non-respiratory signal, data derived from the non-respiratory signal, the audio output signal, data derived from the audio output signal, the secondary audio signal, and/or the GPS derived location information.

In step 720, a kinesthetic output is generated. In many embodiments, the kinesthetic output is generated in response to at least one of the respiratory signal or the non-respiratory signal.

In step 722, a visual output is generated. In many embodiments, the visual output is generated in response to at least one of the respiratory signal and/or the non-respiratory signal.

It should be appreciated that the specific steps illustrated in FIG. 7 provide a particular biofeedback method, according to some embodiments of the present invention. Other sequences of steps may also be performed according to alternative embodiments. For example, alternative embodiments may perform the steps outlined above in a different order. Moreover, the individual steps illustrated in FIG. 7 may include multiple sub-steps that may be performed in various sequences as appropriate to the individual step. Furthermore, additional steps may be added or steps may be removed depending on the particular application. One of ordinary skill in the art would recognize many variations, modifications, and/or alternatives.

Figure 8:
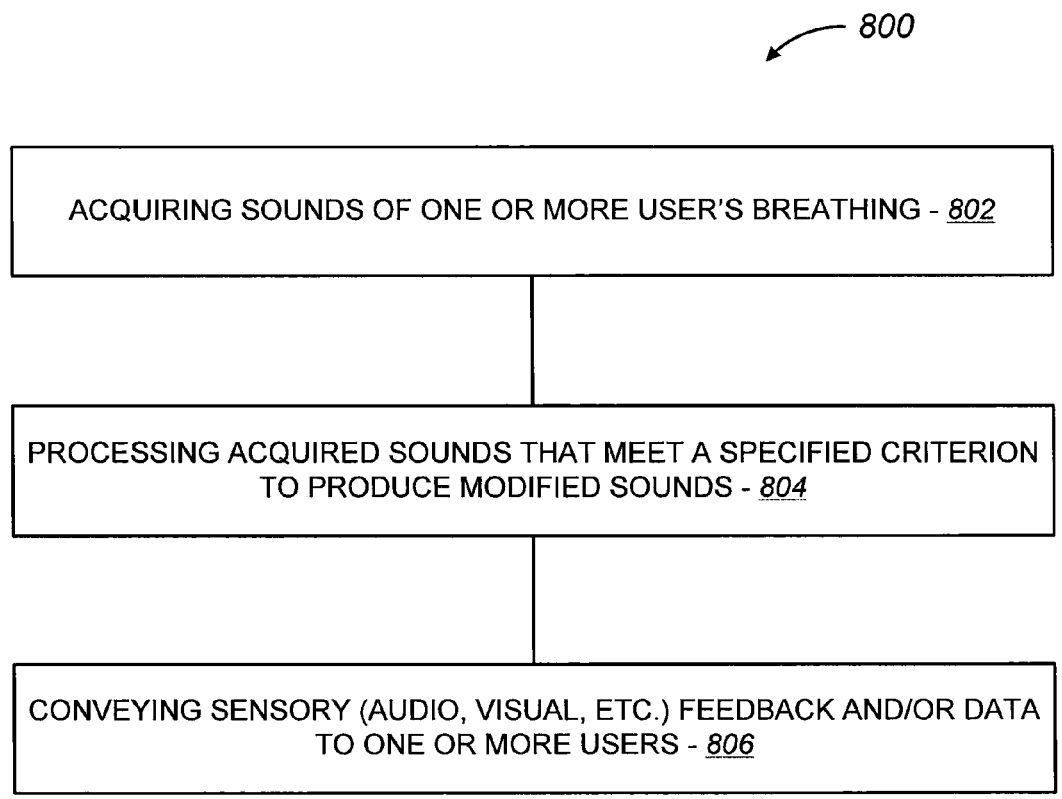
FIG. 8 is a block diagram of a biofeedback method in accordance with many embodiments.

FIG. 8 is a block diagram of a biofeedback method 800 in accordance with many embodiments. The above described biofeedback devices and systems have included many examples and variants which can be configured for use in practicing the method 800.

Step 802 includes acquiring sounds of one or more user's breathing. In many embodiments, the sounds can be acquired using a microphone to convert the sound of the user's respiratory activity into a respiratory signal.

Step 804 includes processing the acquired sounds that meet a specified criterion to produce modified sounds. For example, the acquired sounds can be processed to quantify the sound levels of the user's respiratory activity that exceed a specified sound level. Additionally, the analysis/interpretation can include Fast Fourier Transform (FFT) based analysis; measurement, processing, and/or transformation of amplitude, duration, sound level (dB), sound frequency (Hz), beats, silences, attack, decay, sustain, release, and other audio phenomena and patterns. Further interpretation can include measurement and/or analysis of respiratory aspects, for example, phases of respiration, a respiration cycle, and/or respiration cycles. Phases of respiration can include inhalation, inhalation transition, exhalation, exhalation rest, and the like. Further interpretation and/or analysis can include determination of respiratory rates and parameters; identification of shallow breathing, deep breathing, optimal breathing, anxious breathing, meditative breathing, yogic breathing, snoring, and/or apnea; assessment of performance breathing for activities; and/or any other interpretation and/or analysis of aspects of breathing.

Step 806 includes conveying sensory (audio, visual, etc.) feedback and/or data to one or more users. The conveyed sensory feedback can involve one or more types of sensory feedback.

It should be appreciated that the specific steps illustrated in FIG. 8 provide a particular biofeedback method, according to some embodiments of the present invention. Other sequences of steps may also be performed according to alternative embodiments. For example, alternative embodiments may perform the steps outlined above in a different order. Moreover, the individual steps illustrated in FIG. 8 may include multiple sub-steps that may be performed in various sequences as appropriate to the individual step. Furthermore, additional steps may be added or steps may be removed depending on the particular application. One of ordinary skill in the art would recognize many variations, modifications, and/or alternatives.

Additional Embodiments

Respiratory based biofeedback in accordance with the present invention can be incorporated in additional embodiments. Some examples of these additional embodiments are described below. Each of the below described embodiments can incorporate features and/or functionality of the above described respiratory based biofeedback devices, systems, and/or methods.

In many embodiments, a respiratory based biofeedback head set is provided. The headset includes an audio breath sensor(s) (e.g., a microphone or any other known sensor responsive to a user's respiratory activity) that generates an audio breath signal from a user's respiratory activity. The headset analyzes and interprets the audio breath signal, modifies the audio breath signal based on the analysis/interpretation to generate an audio output signal, and converts the audio output signal into sound waves output to a user of the headset. In many embodiments, the headset includes one or more other physiological sensors (e.g., a heart rate sensor, a brainwave sensor(s), a blood glucose sensor) that generate a corresponding other physiological signal(s) that can be analyzed, interpreted, and/or used to modify the audio breath signal to generate the audio output signal. In many embodiments, the headset generates a visual output and includes a display for the visual output. The headset can generate the visual output in response to the audio breath signal, analysis/interpretation of the audio breath signal, the other physiological signal(s), analysis/interpretation of the other physiological signal(s), and/or the audio output signal. In many embodiments, the headset generates a kinesthetic output and includes a kinesthetic output device (e.g., one of the above described kinesthetic output devices) for the kinesthetic output. The headset can generate the kinesthetic output in response to the audio breath signal, analysis/interpretation of the audio breath signal, the other physiological signal(s), analysis/interpretation of the other physiological signal(s), and/or the audio output signal. In many embodiments, the headset includes a memory that stores data generated in response to the audio breath signal, analysis/interpretation of the audio breath signal, the other physiological signal(s), analysis/interpretation of the other physiological signal(s), the audio output signal, the visual output, and/or the kinesthetic output. In many embodiments, the headset memory can transfer the data to another electronic device (e.g., a computer, a monitor, a kinesthetic output device) for, for example, listening and viewing.

In many embodiments, a signal is generated in response to a user' respiratory activity and the signal is used to generate a audio output, a visual output, and/or a kinesthetic output. The audio output, the visual output, and/or the kinesthetic output may be used to communicate identity and/or feelings, and may be used as art. The audio output, the visual output, and/or the kinesthetic output can include, for example, informational data about the user and the user's respiratory activity. For example, a personalized audio/visual breath interpretation file can be sound, music and/or art generated from the user's respiratory activity. The personalized audio/visual breath interpretation file can be posted on a website; made into a screen saver; embedded into a watch, a piece of jewelry, and/or a pen; made into a greeting card and/or message; framed as an audio/visual picture and/or animation; and/or made into any kind of art, signature and/or visual expression. The signal generated in response to the user's respiratory activity can be made in a wide variety of circumstances (e.g., during an activity, during a period of in-activity, at a particular place, at a particular time, in a particular state of being). Example circumstances include during meditation, during sleep, at a particular time of day, during physical activity, in a detected frame of mind, and/or in a particular venue, etc. The signal generated in response to the user's respiratory activity can be analyzed/interpreted, and the audio output, visual output, and/or kinesthetic output can reflect and/or be generated in response to the analysis/interpretation. The audio output, visual output, and/or kinesthetic output can be played back to the user as a creative reflection of self, to heal in a time of sickness, for meditation, for entertainment, to entrain to an optimal state, and/or at any other time. A user can create one or more personalized audio outputs, visual outputs, and/or kinesthetic outputs. The signal(s) generated in response to the user's respiratory activity, analysis/interpretation of the generated respiratory signal(s), the audio output(s), the visual output(s), and/or the kinesthetic output(s) can be used as representations of identification. The various outputs can be combined in any desired combination. For example, an audio output can be combined with a kinesthetic output, for example, in a stuffed animal with an audio output simulating respiratory activity and kinesthetic output of movement corresponding to the simulated respiratory activity (e.g., expansion/contraction of the stuffed animals chest, purring).

For example, an animatronic toy, vehicle or model and can make sounds and movements that anatomically correspond to the respiratory signal of the user(s), and/or creatively respond the respiratory signal of the user(s). Some examples can include toys or models that breathe as the user(s) breathes, and/or toys or models that make creative gestures and movements accompanied by breathing and/or creative sounds, all responding to the respiratory signal of the user(s). An animatronic toy, vehicle or model can also replicate movements from various known activities in response to the respiratory signal of the user(s). Some examples can include dance, sports, walking, running, jumping, etc. accompanied by breathing and/or creative sounds in response to the respiratory signal of the user(s). All of these examples can incorporate any kind of cue or manipulation of feedback to promote a desired outcome, and be recorded and replayed at a later time. These ideas naturally extend to computer-generated figures in a virtual environment.

In many embodiments, respiratory based biofeedback is presented in the context of a game. The game can, for example, provide training and/or an exercise(s) that increases relaxation and/or performance. A user's respiratory activity, analysis/interpretation of the user's respiratory activity, a signal(s) based on another physiological activity of the user, and/or analysis/interpretation of the signal(s) based on another physiological activity of the user can be used to control a game character(s), a game journey(s), a game challenge(s), and/or a game reward(s). For example, audio, visual, and/or kinesthetic feedback generated in response to a user's respiratory activity can be used to assist a game character(s), an avatar(s), and vehicle(s); facilitate a game journey(s); help overcome a game challenge(s); and/or accelerate a game reward(s). A game can be two dimensional as in computer games and other two-dimensional media, and it can be three dimensional as in board games, computer generated games, or any game that uses three dimensions and/or props and space. There can be two-dimensional or three-dimensional objects that represent players and/or there can be objects that the user(s) interacts with. The three-dimensional objects can respond with audio, visual and/or kinesthetic feedback generated in response to the user's respiratory activity. Haptic inputs can also be used in a game. The haptic inputs can be prompted during any part of the respiratory signal, used to enhance character development, used to provide challenges and rewards, used to affect and be affected by scoring, and the like. A respiratory based biofeedback game(s) can be a single-person game(s), and can include a multi-person game(s), which can be competitive and/or collaborative.

In many embodiments, instruction is added as an audio/visual download based on analysis and interpretation of the signal generated in response to the user's respiratory activity. The analysis and interpretation can be performed by a physician, therapist, trainer, coach, teacher, and/or other suitable provider, as well as by an automated and/or monitored computerized process.

In many embodiments, there is an additional inquiry input. For example, questions are asked and data is collected pertaining to the user's contact information, interests, physical health, mental health, emotional health, and spiritual health, habits, etc. The data is analyzed, interpreted and fed back to the user along with the respiratory based feedback and/or data.

In many embodiments, there are multi-media capabilities. For example, audio, visual, and/or kinesthetic processors and outputs can be used. Audio, visual, and/or kinesthetic output and/or data can be used to create templates. Existing audio, visual, and/or kinesthetic data can be obtained from existing sources comprising any network or technology.

In many embodiments, a non-respiratory signal is generated in response to non-respiratory activity of a user. For example, behavioral parameters and physiological sensors can be used to generate a signal in response to a pheromone level(s) of the user. An olfactory generator can also be used to output a fragrance to the user as a form of feedback.

In many embodiments, there is an olfactory based sensor/parameter and/or an olfactory generator. The sense of smell can be employed, for example, as part of a multisensory input and output. For example, a respiratory-based biofeedback device/system can include an olfactory-based sensor/parameter and a respiration sensor. A user may be able to use such a device/system to observe a relationship(s) that may exist between a pheromone level(s) of the user and the user's respiratory activity. Such a device/system may have practical applications, for example, as a means of testing and developing medical, pharmaceutical, and industrial protocols. Such a device/system may be used to, for example, develop breathing protocols to optimize a user's pheromone level(s). A user of such a device/system may be able develop intuitive and/or cognitive regulation of the user's pheromone(s). Such a device/system may be useful to determine a relationship(s) between a scent(s), a substance(s), and the user's respiratory activity, which may be useful in the development of perfumes and the uses of scents in research, medicine, industry, personal use, well-being, and the like.

In many embodiments, patterns obtained from the sounds of a user's respiratory activity are used as an algorithm to generate sound, music, two-dimensional art, and/or three-dimensional art. Such generative sound/art can create physiological coherence and harmony. The generative sound/art feedback can create optimal physiological responses and body/mind harmony in participants, as well as other viewers. Generative sound/art based on breathing and other physiological patterns mirror one's physiological responses in a less direct way, thereby, averting self-judgment, comparisons and the like, making optimal breathing and physiological states easier to access and experience.

All patents and publications referred to above are incorporated by reference herein.

As will be understood by those skilled in the art, the present invention may be embodied in other specific forms without departing from the essential characteristics thereof. In many embodiments, devices and apparatuses are contemplated employing designs which practice each of the above biofeedback methods. These can also perform any one or a combination of the above-described associated embodiments. Those skilled in the art will recognize, or be able to ascertain using no more than routine experimentation, many equivalents to the specific embodiments of the invention described herein. Such equivalents are intended to be encompassed by the following claims.

What is claimed is:

1. A biofeedback method, comprising:
   producing a respiratory signal in response to a user's respiratory activity;
   generating an audio output signal comprising a modified version of the respiratory signal, wherein a modification to the respiratory signal changes based on an output of a state machine, wherein the state machine is implemented on a digital signal processor and wherein the state machine controls an audio processor on the digital signal processor and is operable to:
      perform calibration during a calibrate state of the state machine using the respiratory signal, wherein the calibration comprises setting a low threshold and a high threshold; and
      responsive to results from the calibration, detecting breaths of the user in a breath detection state of the state machine using the low threshold and the high threshold established during the calibrate state, wherein the detecting comprises detecting a plurality of troughs and peaks associated with a respective breath of the breaths; and
   converting the audio output signal into sound waves output to the user to provide biofeedback using a biofeedback device in real time responsive to a mode of operation selected by the user and user respiratory activity as measured by the detected breaths.

2. The method of claim 1, wherein the respiratory signal is modified based on a characteristic other than intensity.

3. The method of claim 1, wherein the respiratory signal is modified based on a numerical calculation.

4. The method of claim 1, wherein the respiratory signal is modified to at least one of enhance, accentuate, or amplify a portion of the respiratory signal.

5. The method of claim 1, wherein the audio output signal is generated by using a first device, and the method further comprises transmitting at least one of the respiratory signal or the audio output signal to a second device for at least one of processing, analysis, or storage in memory.

6. The method of claim 5, wherein the transmission occurs over a communication network.

7. The method of claim 1, wherein the biofeedback provides at least one of education, behavioral modification, stress reduction, snoring reduction, or training to the user.

8. The method of claim 7, wherein the biofeedback provides fitness training to the user.

9. The method of claim 1, wherein the respiratory signal is modified to accentuate a portion of the respiratory signal having an intensity level above a specified intensity level.

10. The method of claim 1, further comprising storing data in a memory device, the data comprising at least one of:
    the respiratory signal;
    data derived from the respiratory signal;
    the audio output signal; or
    data derived from the audio output signal.

11. The method of claim 1, wherein producing a respiratory signal comprises converting sound of the user's respiratory activity into the respiratory signal.

12. The method of claim 11, wherein the generated audio output signal comprises the respiratory signal modified to increase the volume level of a portion of the respiratory signal where the volume level exceeds a specified volume level.

13. The method of claim 1, further comprising: producing a secondary audio signal; and adding the secondary audio signal to the audio output signal.

14. The method of claim 1, further comprising: determining one or more locations for the user; and storing the one or more locations in a memory device.

15. The method of claim 1, further comprising generating a kinesthetic output in response to at least one of the respiratory signal or the audio output signal.

16. The method of claim 1, further comprising generating a visual output in response to at least one of the respiratory signal or the audio output signal.

17. An article comprising a non-transitory computer storage medium having instructions stored thereon, which instructions, when executed by a processor, result in the processor performing the following method:
    receiving a respiratory signal in response to a user's respiratory activity;
    generating an audio output signal comprising a modified version of the respiratory signal, wherein a modification to the respiratory signal changes based on an output of a state machine, wherein the state machine is implemented on a digital signal processor and wherein the state machine controls an audio processor on the digital signal processor and is operable to:
  perform calibration during a calibrate state of the state machine using the respiratory signal, wherein the calibration comprises setting a low threshold and a high threshold; and
  responsive to results from the calibration, detecting breaths of the user in a breath detection state of the state machine using the low threshold and the high threshold established during the calibrate state, wherein the detecting comprises detecting a plurality of troughs and peaks associated with a respective breath of the breaths; and
converting the audio output signal into sound waves output to the user to provide biofeedback in real time responsive to a mode of operation selected by the user and user respiratory activity as measured by the detected breaths.

18. A biofeedback method, comprising:
producing a respiratory signal in response to a user's respiratory activity;
generating a non-respiratory signal in response to a non-respiratory physiological activity of the user;
  quantifying an aspect of the non-respiratory signal;
  generating an audio output signal comprising the respiratory signal modified in response to the quantified aspect of the non-respiratory signal and an output of a state machine, wherein the state machine is implemented on a digital signal processor and wherein the state machine controls an audio processor on the digital signal processor and is operable to:
    perform calibration during a calibrate state of the state machine using the respiratory signal, wherein the calibration comprises setting a low threshold and a high threshold; and
    responsive to results from the calibration, detecting breaths of the user in a breath detection state of the state machine using the low threshold and the high threshold established during the calibrate state, wherein the detecting comprises detecting a plurality of troughs and peaks associated with a respective breath of the breaths; and
converting the audio output signal into sound waves output to the user in real time responsive to a mode of operation selected by the user and user respiratory activity as measured by the detected breaths.

19. The method of claim 18, further comprising storing data in a memory device, the data comprising at least one of:
  the respiratory signal;
  data derived from the respiratory signal;
  the non-respiratory signal;
  data derived from the non-respiratory signal; the audio output signal; or
  data derived from the audio output signal.

20. The method of claim 18, wherein producing a respiratory signal comprises converting sound of the user's respiratory activity into the respiratory signal.

21. The method of claim 18, further comprising:
producing a secondary audio signal; and
adding the secondary audio signal to the audio output signal.

22. The method of claim 18, further comprising: determining one or more locations for the user; and storing the one or more locations in a memory device.

23. The method of claim 18, further comprising generating a kinesthetic output in response to at least one of the respiratory signal, the non-respiratory signal, or the audio output signal.

24. The method of claim 18, further comprising generating a visual output in response to at least one of the respiratory signal, the non-respiratory signal, or the audio output signal.

25. An article comprising a non-transitory computer storage medium having instructions stored thereon, which instructions, when executed by a processor, result in the processor performing the following method:
  receiving a respiratory signal in response to a user's respiratory activity;
  generating a non-respiratory signal in response to a non-respiratory physiological activity of the user;
  quantifying an aspect of the non-respiratory signal;
  generating an audio output signal comprising the respiratory signal modified in response to the quantified aspect of the non-respiratory signal and an output of a state machine, wherein the state machine is implemented on a digital signal processor and wherein the state machine controls an audio processor on the digital signal processor and is operable to:
    perform calibration during a calibrate state of the state machine using the respiratory signal, wherein the calibration comprises setting a low threshold and a high threshold; and
    responsive to results from the calibration, detecting breaths of the user in a breath detection state of the state machine using the low threshold and the high threshold established during the calibrate state, wherein the detecting comprises detecting a plurality of troughs and peaks associated with a respective breath of the breaths; and
converting the audio output signal into sound waves output to the user in real time responsive to a mode of operation selected by the user and user respiratory activity as measured by the detected breaths.

26. A biofeedback system, comprising:
  a respiratory sensor configured to generate a respiratory signal in response to a user's respiratory activity;
  a processing unit communicatively coupled with the respiratory sensor and comprising a digital signal processor and a tangible medium comprising instructions that when executed cause the digital signal processor to generate an audio output signal comprising a modified version of the respiratory signal wherein a modification to the respiratory signal changes based on an output of a state machine, wherein the state machine is implemented on the processing unit and is operable to:
    perform calibration during a calibrate state of the state machine using the respiratory signal, wherein the calibration comprises setting a low threshold and a high threshold; and
    responsive to results from the calibration, detecting breaths of the user in a breath detection state of the state machine using the low threshold and the high threshold established during the calibrate state, wherein the detecting comprises detecting a plurality of troughs and peaks associated with a respective breath of the breaths; and
  an audio output device communicatively coupled with the processing unit and configured to convert the audio output signal to sound waves output to the user to provide biofeedback in real time responsive to a mode of operation selected by the user and user respiratory activity as measured by the detected breaths.

27. The system of claim 26, wherein the respiratory signal is modified to accentuate a portion of the respiratory signal having an intensity level above a specified intensity level.

28. The system of claim 26, wherein the respiratory sensor comprises a microphone.

29. The system of claim 28, wherein the generated audio output signal comprises the respiratory signal modified to increase the volume level of portions of the respiratory signal where the volume level exceeds a specified volume level.

30. The system of claim 28, wherein the microphone is operable acquire breath sounds, and wherein the microphone is further operable to maximize sensitivity to breath sounds while rejecting unwanted ambient sounds.

31. The system of claim 28, wherein the microphone is selected from a group consisting of: surface stethoscope microphone and a condenser microphone.

32. The system of claim 26, comprising an audio source configured to generate a secondary audio signal that is added to the audio output signal.

33. The system of claim 26, wherein:
the system comprises a kinesthetic output device communicatively coupled with the processing unit; and
the tangible medium comprises instructions that when executed cause the processor to generate a kinesthetic output for the kinesthetic output device in response to at least one of the respiratory signal or the audio output signal.

34. The system of claim 26, wherein:
the system comprises a display communicatively coupled with the processing unit; and
the tangible medium comprises instructions that when executed cause the processor to generate a visual output for the display in response to at least one of the respiratory signal or the audio output signal.

35. The system of claim 26, wherein:
the system comprises:
a location-determining device communicatively coupled with the processing unit and configured to determine one or more locations for the user, and
a memory device communicatively coupled with the processing unit; and
the tangible medium comprises instructions that when executed cause the processor to store the one or more locations in the memory device.

36. The system of claim 26, wherein:
the system comprises a memory device communicatively coupled with the processing unit; and
the tangible medium comprises instructions that when executed cause the processor to store data in the memory device, the data comprising at least one of
the respiratory signal;
data derived from the respiratory signal;
the audio output signal; or
data derived from the audio output signal.

37. The system of claim 26, further comprising a biofeedback headset, wherein the biofeedback headset comprises the respiratory sensor, the processing unit, and the audio output device.

38. The system of claim 37, wherein the biofeedback headset comprises other physiological sensors selected from the group consisting of: a heart rate sensor, a brainwave sensor, a blood glucose sensor, a temperature sensor, a muscle tension sensor, an arterial pressure sensor, an oxygen sensor, and a glucose sensor.

39. The system of claim 37, wherein the biofeedback headset comprises a display for a visual output, and further wherein, the biofeedback headset is operable to generate the visual output.

40. The system of claim 37, wherein the biofeedback headset comprises a kinesthetic output device operable to generate a kinesthetic output.

41. The system of claim 37, further comprising a mobile device, wherein the mobile device comprises the biofeedback headset, and further, wherein the mobile device comprises a display.

42. The system of claim 41, wherein the mobile device is communicatively coupled with a server via a communication link.

43. The system of claim 42, wherein the server is operable to transmit group based data to said mobile device, wherein the group based data comprises data regarding a comparison of a respiratory activity of a user with a group of other users.

44. The system of claim 26, wherein the audio output device comprises binaural earphones.

45. The system of claim 26, wherein the mode of operation is selected from a group consisting of: basic mode, stress reduction mode; anti-snoring mode; and a fitness training mode.

46. The system of claim 45, wherein the mode of operation is basic mode, wherein in the basic mode the user can set a volume of the audio output signal and choose an effects preset.

47. The system of claim 45, wherein the mode of operation is anti-snoring mode, and wherein in anti-snoring mode the system is configured to increase an output volume of the audio output signal as an input volume of the user's respiratory activity increases, and wherein the mode of operation reverts to the basic mode when the input volume subsides.

48. The system of claim 45, wherein the mode of operation is stress reduction mode, and wherein in the stress reduction mode the system is configured to comprise an audio source configured to generate a secondary audio signal that is added to the audio output signal, and wherein the user can select the secondary audio signal from pre-programmed options.

49. The system of claim 45, wherein the mode of operation is fitness training mode, wherein in the fitness training mode the system is configured to add a sound of a pulse to the audio output signal, wherein the pulse is operable to act as a cue for the user to breathe at a certain rate.

* * * * *